US010274501B2

(12) United States Patent
Yin et al.

(10) Patent No.: US 10,274,501 B2
(45) Date of Patent: Apr. 30, 2019

(54) IMMUNOGENICITY ASSAY

(71) Applicant: ANP Technologies, Inc., Newark, DE (US)

(72) Inventors: Ray Yin, Newark, DE (US); Jing Pan, Newark, DE (US); Yli Remo Vallejo, Newark, DE (US); Thomas Small, Newark, DE (US); Dujie Qin, Wilmington, DE (US); De Chen, Newark, DE (US)

(73) Assignee: ANP Technologies, Inc., Newark, DE (US)

( * ) Notice: Subject to any disclaimer, the term of this patent is extended or adjusted under 35 U.S.C. 154(b) by 384 days.

(21) Appl. No.: 15/143,576

(22) Filed: Apr. 30, 2016

(65) Prior Publication Data

US 2016/0327569 A1    Nov. 10, 2016

Related U.S. Application Data

(60) Division of application No. 14/828,379, filed on Aug. 17, 2015, now Pat. No. 9,329,187, which is a continuation of application No. 13/382,288, filed as application No. PCT/US2010/034042 on May 7, 2010, now abandoned.

(60) Provisional application No. 61/332,386, filed on May 7, 2010, provisional application No. 61/297,088, filed on Jan. 21, 2010, provisional application No. 61/223,725, filed on Jul. 8, 2009.

(51) Int. Cl.
G01N 33/50    (2006.01)
G01N 33/68    (2006.01)
G01N 33/558   (2006.01)
G01N 33/543   (2006.01)

(52) U.S. Cl.
CPC ... *G01N 33/6854* (2013.01); *G01N 33/54306* (2013.01); *G01N 33/558* (2013.01)

(58) Field of Classification Search
None
See application file for complete search history.

(56) References Cited

U.S. PATENT DOCUMENTS

| 5,714,166 | A   | 2/1998 | Tomalia et al. |
| 7,229,771 | B2  | 6/2007 | Hornauer et al. |
| 7,547,557 | B2  | 6/2009 | LaBorde et al. |
| 8,216,793 | B2  | 7/2012 | Lubich et al. |
| 2003/0129677 | A1* | 7/2003 | Martens ........... G01N 33/57484 435/7.23 |
| 2006/0019406 | A1 | 1/2006 | Wei et al. |
| 2006/0041058 | A1 | 2/2006 | Yin et al. |

FOREIGN PATENT DOCUMENTS

EP    1098198    5/2001

OTHER PUBLICATIONS

Maggio et al., Enzyme Immunoassay, CRC Press Inc., 1987, pp. 186-187. (Year: 1987).*
Overton, "Ligand binding . . . validation issues," Chromatog 55, Suppl. s101-106, 2002.
Geng et al., "Validation . . . antibodies," J Pharm Biomed Anal 39, 364-375, 2005.

* cited by examiner

*Primary Examiner* — Gary Counts
(74) *Attorney, Agent, or Firm* — MDIP LLC

(57) ABSTRACT

Assays for detecting antibodies to pharmaceutical preparations, food allergens and environmental allergens are described.

20 Claims, 33 Drawing Sheets

Figure 3. Dose Response Curve for an LFA Immunogenicity Bridging Assay

Figure 4. Dose Response Curve for an Immunogenicity LFA for the Detection of Antibodies to 40 kDa PEG Figure 5. Drug Depletion Assay for 40 kDa PEG Immunogenicity LFA Figure 6. Screening of 50 Normal Human Serum Samples with 40 kDa PEG Immunogenicity LFA.

Figure 7. Retesting of Borderline Positive Human Samples in a Drug Depletion Assay. .

Figure 8. Dose Response Curve for an Immunogenicity LFA for the Detection of Antibodies to Glucagon Figure 9. Drug Depletion Assay for the Glucagon Immunogenicity LFA Figure 10. Screening of 50 Normal Human Serum Samples with the Glucagon Immunogenicity LFA Figure 11. Retesting of Apparent Positive Normal Human Samples in a Drug Depletion Assay Figure 12. Dose Response Curve for an Immunogenicity LFA for the Detection of Antibodies to GLP-1

Figure 13. Drug Depletion Assay for the GLP-1 Immunogenicity LFA

Figure 14. Screening of 50 Normal Human Serum Samples with the GLP-1 Immunogenicity LFA Figure 15. Retesting of Apparent Positive Normal Human Samples in a Drug Depletion Assay Figure 16. Screening 25 Obese Human Serum Samples with the GLP-1 Immunogenicity LFA Figure 17. Screening of 25 Obese Human Serum Samples with the GLP-1 Immunogenicity LFA Figure 18. Retesting of an Apparent Positive Obese Human Patient Sample in a Drug Depletion Assay Figure 19. Design of an LFA for the Identification of IgG (or Other) Isotype ADAs Figure 20. Reaction Schematic of an LFA for the Identification of IgM ADAs Figure 21. Reaction Schematic of an LFA for the Identification of IgA ADAs Figure 22. Reaction Schematic of an LFA for the Identification of IgE (or IgD) ADAs Figure 23. Alternative Reaction Schematic for an LFA for the Identification of IgG (or Other Isotype) ADAs Using Unlabeled Drug Figure 24. Alternative Reaction Schematic of an LFA for the identification of IgE (or Other Isotype) ADAs

IMMUNOGENICITY ASSAY

FIELD OF THE INVENTION

The present invention relates in part to the measurement of drugs and antibodies to drugs, food antigens and other environmental antigen, such as those which are unmodified and modified biological molecules, in host animals and patients. The use of for example, proteins and nucleic acids as drugs, such as recombinant proteins, peptides, antibodies, binding receptors, DNA, small interfering RNA (siRNA), micro RNA (miRNA), and RNA interference (RNAi), has proliferated in the last two decades. Because of size, charge and content, for example, such molecules are commonly immunogenic eliciting antibodies thereto in a host animal or a human patient. Many such large molecules are manipulated to contain substituents in an effort to reduce immunogenicity. Hence, many such large molecule drugs are composed of multiple elements, the drug per se and other substituents. However, those substituents also may be immunogenic. In addition, this invention disclosure also covers those assays for the detection of specific immunoglobulin isotypes, such as, IgG, IgM, IgA, IgD and IgE, or subtypes thereof, that are specific for a drug or a composite drug, as well as to the particular substituents attached to a drug, such as, a water soluble polymer.

BACKGROUND OF THE INVENTION

Developers of therapeutic biologic-based pharmaceuticals seek to minimize potential immunogenicity thereof, for example, by humanization, cloaking immunogenic sites or developing chimeric constructs by combining alleged minimally immunogenic or non-immunogenic human sequences with active domains from, for example, non-human sources which are potentially immunogenic. However, in spite of those measures, such drugs or composite drugs remain immunogenic or the potential remains for patients to develop an immune reaction to the administered drug, rendering the drug initially ineffective, progressively ineffective and/or life-threatening, because of, for example, an anaphylactic reaction thereto.

It is therefore important to measure the immunogenicity of drugs, for example, during the development process to optimize drug design. Also, such assays can be used to determine the responsiveness of a recipient to a drug, either prior to exposure or to monitor a patient during a course of treatment. Thus, an assay that detects anti-drug antibodies (ADA), for example, in the serum or plasma of host animals or patients undergoing treatment, can be used for those reasons.

Some current methods for measuring drug immunogenicity employ enzyme-linked immunosorbent assay (ELISA) materials and methods. Those assays generally utilize a double antigen bridging format wherein the drug is coated onto a solid phase, such as, a well in a microtiter plate, and a labeled version of the same drug is dissolved in a liquid medium. The label can consist of a signal-developing enzyme or a binding moiety that can complex with a binding partner labeled with a signal-developing enzyme. The ADA in the patient sample can then form a bridge complex wherein one binding site attaches to the coated antigen and another binding site binds the labeled drug. After washing and addition of substrate reagents, the wells containing ADA will develop a signal associated with the bound enzyme.

Surface plasmon resonance (SPR) assays are also used for the determination of immunogenicity using a direct and label-free assay format.

But those assays suffer from being labor-intensive and time-intensive as well as requiring complex and expensive equipment. In some cases, a sample dilution step is required to reduce background (i.e., for SPR and ELISA assays) or multiple washing steps are needed to separate bound from free antibodies and antigens (i.e., for ELISA). The washing step(s) can remove low affinity and low avidity ADA, for example, as antibodies have different on-rates and off-rates, detection of antibodies with fast off rates may not be detected due to extensive washing. Further, the sample dilution step can result in the identification of a negative response when patients may actually possess low, but clinically relevant, levels of ADAs.

SUMMARY OF THE INVENTION

To overcome the shortcomings in the art of detecting antibody to drugs, food antigens, environmental antigens and other antigens in general, the instant invention relates to an immunochromatographic assay, also known as a lateral flow assay (LFA) for the detection of such antibody. The assays are directed in part to detecting antibodies that specifically bind a drug (ADA). The LFA can be configured to comprise drug-ADA-drug bridge sandwich assays, competitive assays and direct serologic assays (i.e., drug molecule is immobilized on a solid surface through either direct or indirect linkages, followed by detecting any bound ADA with, for example, direct or indirectly labeled anti-immunoglobulin).

The direct and indirect linkages can be covalent or non-covalent. In addition, the indirect linkages can be formed through a reaction between two members of a binding pair, wherein a member of a binding pair can include an antibody or an antigen-binding portion thereof, an antigen, an avidin/streptavidin/neutravidin, a biotin, a dinitrophenol (DNP), an anti-DNP antibody, a digoxin, an anti-digoxin antibody, a digoxigenin, an anti-digoxigenin antibody, a hapten, an anti-hapten antibody, a polysaccharide, a polysaccharide binding moiety, such as a lectin, a receptor, a fluorescein, an anti-fluorescein antibody, a complementary DNA, an RNA etc.

Advantageously, the instant assays do not require sample dilution, which reduces the ability of conventional methods to detect low titers of the antibodies of interest, such as, ADA. Also, the instant assays do not require one or more wash steps. That enhances the likelihood of detecting antibodies with a wide range of affinities, particularly low affinity or low avidity ADA.

The instant assays also can employ certain dendrimers, dendrigrafts, hyperbranched polymers, dendritic polymers, star-shaped polymers, comb-shaped polymers, and randomly branched polymers as a component of a reagent of interest. All of these polymers are generally referred to as branched polymers in this invention. Such a manipulation often increases the availability of antigenic epitopes on the drug of interest, enabling more efficient detection of such antibodies and reduces or removes the high dose hook effect that challenges other assays and assay formats.

In a similar manner, the performance of immunogenicity assays of various designs in conventional ELISA microplate and bead assay formats can also be enhanced by the use of the same branched polymers as a component on the reagents employed in such assays for the detection of such antibodies.

A further application of the invention is in the identification of the immunoglobulin isotype that constitutes the immunogenic antibody response in the patient sample to such antigens.

In one embodiment, an immunoassay method for detecting the presence of an antibody against a drug of interest (DOI), such as an ADA, or an antibody to a food antigen (FA) or to an environmental antigen (EA) is disclosed including contacting at least one immunochromatographic solid phase with a sample on a first solid phase, such as a strip, in a proximal region thereof, where the sample includes at least one antibody in a mobile phase; allowing a mobilized antibody to flow from the proximal region into a distal region of the solid phase, where the distal region includes an immobilized capture agent at a capture site or test site in a distal region of the solid phase, and where the capture agent immobilizes the antibody in a complex, wherein the antibody complex includes a first DOI, FA or EA moiety bound to a first antigen binding region of the antibody and the first DOI, FA or EA moiety comprises a means to bind a reporter moiety; and detecting reporter binding at the capture site, where the detecting of reporter levels correlates with the presence of an antibody against the DOI, FA or EA in the sample. In some embodiments, the sample is applied to a second solid phase, such as a pad, which is in fluid communication with the first solid phase. In a related aspect, at least one strip/test is contained in a multi-strip/multi-test immunochromatographic solid phase device.

In one aspect, the first DOI, FA or EA moiety and the reporter are connected through a first binding pair, and where the DOI, FA or EA moiety includes a first cognate tag, such as a first member of a binding pair, and the reporter comprises a second cognate tag, or a second member of the first binding pair.

In a related aspect, the capture agent is the DOI, FA or EA, or an antibody or binding partner directed against the DOI, FA or EA.

In one aspect, the capture agent is a member of a second binding pair. In a related aspect, the antibody further includes a second DOI, FA or EA moiety bound to a second antigen binding region, and where the second DOI, FA or EA moiety includes a first cognate tag, or a first member, of a second binding pair, which capture agent (i.e., a second cognate tag or a second member of the second binding pair) specifically binds to the first cognate tag of the second binding pair.

In a further related aspect, the first and/or second cognate tags further include a branched polymer or a dendritic polymer, such as a symmetrically or an asymmetrically branched polymer. In a related aspect, the symmetrically branched polymers include star-shaped polymers, comb-shaped polymers, dendrimers, starburst dendrimers, combburst dendrigrafts, and/or hypercombbranched polymers. In a further related aspect, the asymmetrically branched polymers include polylysine dendrimers or randomly branched polymers.

In another aspect, the method further includes mixing the sample with the first and second DOI, FA or EA moieties prior to contacting the solid phase.

In one aspect, the capture agent is a DOI, FA or EA. In a related aspect, the method further includes prior to contacting, mixing the sample with the reporter, where the reporter includes a first cognate tag of a first binding pair, where a DOI, FA or EA moiety includes a second cognate tag of a first binding pair. The DOI, FA or EA moiety can be releasably immobilized on the second or a third solid phase which is in fluid communication between the first and/or second solid phase. Thus, the DOI, FA or EA moiety can be releasably immobilized on the second solid phase for accepting the sample or be present on a third solid phase which is in fluid communication with the first and second solid phases.

In another aspect, the first and/or second cognate tags further include symmetrically or asymmetrically branched polymers. In a related aspect, the symmetrically branched polymers include star-shaped polymers, comb-shaped polymers, dendrimers, starburst dendrimers, combburst dendrigrafts, and/or hypercombbranched polymers.

In one aspect, the first cognate tag is a hapten. In a related aspect, the hapten includes dinitrophenol (DNP), digoxigenin, digoxin, fluorescein, thyroxine, tetrahydrocannabinol (THC), morphine, amphetamine, heroin, and barbiturates. In another aspect, the binding pair includes an antibody or an antigen-binding portion thereof and an antigen, an avidin/streptavidin/neutravidin and a biotin, a DNP and an anti-DNP antibody, a digoxin and an anti-digoxin antibody, a digoxigenin and an antidigoxigenin antibody, a hapten and an anti-hapten antibody, a polysaccharide and a polysaccharide binding moiety, a lectin and a receptor, a ligand and a receptor, a fluorescein and an anti-fluorescein antibody, and complementary nucleic acids.

In one aspect, the reporter includes, but is not limited to, an enzyme, a ferritin, a fluorescent or colored micro- or nanoparticle/bead, a colloid metal, a quantum dot, a magnetic particle, an up-converting phosphorescent particle, an electrochemiluminescent molecule, compounds containing a transition metal, and/or a compound containing a lanthanide metal. In a related aspect, the transition metal is Ru or Os. In a further related aspect, the lanthanide metal is Ce, Pr, Nd, Pm, Sm, Eu, Gd, Tb, Dy, Ho, Er, Tm, Yb, or Lu.

In one aspect, the DOI includes organic compounds, polypeptides, antibodies, monoclonal antibodies, immunoglobulins, and antigen-binding portions thereof, polynucleotides, siRNA, RNAi, miRNA, lipids, saccharides, polysaccharides, and combinations thereof.

In another aspect, the antibody has an isotype including IgG, IgM, IgA, IgE, and IgD.

In one aspect, the ADA binds to a drug substituent. In a related aspect, the drug substituent includes a charged group, an ester group, a glycan, a carbohydrate, a functional group, a ketone, a carbonyl group, a hydrocarbon, a lipid, and/or a synthetic polymer. In a related aspect, the synthetic polymer is polyethylene glycol (PEG) or polyethyleneoxide (PEO).

In another aspect, at least one multi-strip immunochromatographic solid phase is contained within a holding device or holder. In one aspect, a plurality of multi-strip immunochromatographic solid phases are contained within a holding device or holder. In a related aspect, each multi-strip immunochromatographic solid phase includes a separate reporter which binds to a different Ig isotype. In a further related aspect, the holding means includes a tissue culture plate substratum, a multi-well plate substratum or a combination thereof.

In one aspect, the solid phase includes a membrane such as nitrocellulose, glass fiber, cotton, and nylon (polyamide) membranes, a glass micro/nanochannel, a plastic micro/nanochannel a natural wick, a synthetic wick, microbead particles, nanobead particles or a combination thereof.

In another aspect, the holding means includes a tissue culture plate substratum, a multi-well plate substratum or a combination thereof.

In another embodiment, an immunoassay method for determining the isotype of an antibody against a drug of interest (DOI), FA or EA is disclosed including contacting a plurality of multi-strip immunochromatographic solid phases with a sample on a first solid phase, such as a strip, in proximal regions thereof, where the sample includes at least one antibody in a mobile phase, and where the first solid phase contains a capture agent which selectively binds a specific Ig isotype at a capture site or test site distally on said first solid phase; allowing a mobilized antibody to flow from the proximal regions into distal regions of the solid phase, where the distal region includes the capture agent at the test site, and where the capture agent immobilizes the antibody in a complex including the select Ig isotype, whereby the antibody includes a first DOI, FA or EA moiety bound to a first antigen binding region of the antibody and the first DOI, FA or EA moiety comprises a means to bind a reporter moiety; and determining or detecting reporter binding at the capture site on the solid phase, where the determining of the amount or reporter at the capture site correlates with the presence of one or more antibody Ig isotypes in the sample.

In one aspect, the first DOI, FA or EA moiety and the reporter are connected through a first binding pair, and where the DOI FA or EA moiety includes a first cognate tag, or member of the first binding pair, and the reporter includes a second cognate tag, or second member, of the first binding pair.

In a related aspect, the capture agent is the DOI, FA or EA, or an antibody or binding pair directed against the DOI, FA or EA.

In another aspect, the capture agent is antibody member of a second binding pair. In a related aspect, the antibody further includes a second DOI, FA or EA moiety bound to a second antigen binding region, and where the second DOI, FA or EA moiety includes a first cognate tag, or first member, of a second binding pair, which capture agent (i.e., a second cognate tag or a second member of the second binding pair) specifically binds to the first cognate tag for the second binding pair. In another related aspect, the first and/or second cognate tags further include symmetrically or asymmetrically branched polymers. In a related aspect, the symmetrically branched polymers include star-shaped polymers, comb-shaped polymers, dendrimers, starburst dendrimers, combburst dendrigrafts, and/or hypercomb-branched polymers. In a further related aspect, the asymmetrically branched polymers include polylysine dendrimers or randomly branched polymers.

In one aspect, the method further includes mixing the sample with the first and second DOI, FA or EA moieties prior to contacting the solid phases. In another aspect, a plurality of multi-strip immunochromatographic solid phases are contained within a holding means. In one aspect, the solid phases include a membrane, a natural wick, a synthetic wick, microbead particles, nanobead particles or a combination thereof.

In another aspect, the holding means includes a tissue culture plate substratum, a multi-well plate substratum or a combination thereof.

In one aspect, the first cognate tag is a hapten. In a related aspect, the hapten includes DNP, digoxigenin, digoxin, fluorescein, thyroxine, THC, morphine, amphetamine, heroin, and barbiturates. In another aspect, the binding pair includes an antibody or an antigen-binding portion thereof and an antigen, an avidin/streptavidin/neutravidin and a biotin, a dinitrophenol (DNP) and an anti-DNP antibody, a digoxin and an anti-digoxin antibody, a digoxigenin and an anti-digoxigenin antibody, a hapten and an anti-hapten antibody, a polysaccharide and a polysaccharide binding moiety, a lectin and a receptor, a ligand and a receptor, a fluorescein and an anti-fluorescein antibody, and complementary nucleic acids.

In one aspect, the reporter includes, but is not limited to, an enzyme, a ferritin, a fluorescent or colored microparticle/bead or nanoparticle/bead, a colloid metal, a quantum dot, a magnetic particle, an up-converting phosphorescent particle, an electrochemiluminescent molecule, such as Ru containing molecules, compounds containing a transition metal, and compound containing a lanthanide metal.

In one embodiment, an immunoassay method for detecting the presence of an antibody against a drug of interest (DOI), FA or EA is disclosed including contacting at least one multi-strip immunochromatographic solid phase with a sample on the solid phase in a proximal region thereof, where the sample includes at least one antibody in a mobile phase; allowing a mobilized antibody to flow from the proximal region into a distal region of the solid phase, where the distal region includes an immobilized DOI, FA or EA at a distal region of the solid phase (the capture site or test site), and where the DOI, FA or EA immobilizes the antibody, whereby the antibody includes a first DOI, FA or EA moiety bound to a first antigen binding region of the antibody and the first DOI, FA or EA moiety comprises a means for binding a reporter moiety; and detecting the presence of and levels of reporter binding to the immobilized DOI FA or EA, where the detecting of levels of reporter binding correlates with the presence of an antibody against the DOI, FA or EA.

In one aspect, the first DOI, FA or EA moiety and the reporter are connected through a first binding pair, and where the DOI, FA or EA moiety includes a first cognate tag and the reporter includes a second cognate tag for the first binding pair. In another aspect, the method further includes prior to conducting the assay, mixing the sample with the reporter, where the reporter includes a first cognate tag of a first binding pair, where the DOI, FA or EA moiety includes a second cognate tag of a first binding pair, and where the DOI, FA or EA moiety is releasably immobilized on the second or a third solid phase all of which are in fluid communication and with the first solid phase. In a related aspect, the first and/or second cognate tags further comprise symmetrically or asymmetrically branched polymers.

BRIEF DESCRIPTION OF THE FIGURES

The following descriptions of the figures relate to non-limiting examples that depict various embodiments exemplifying the present invention.

DETAILED DESCRIPTION OF THE INVENTION

Figure 1:
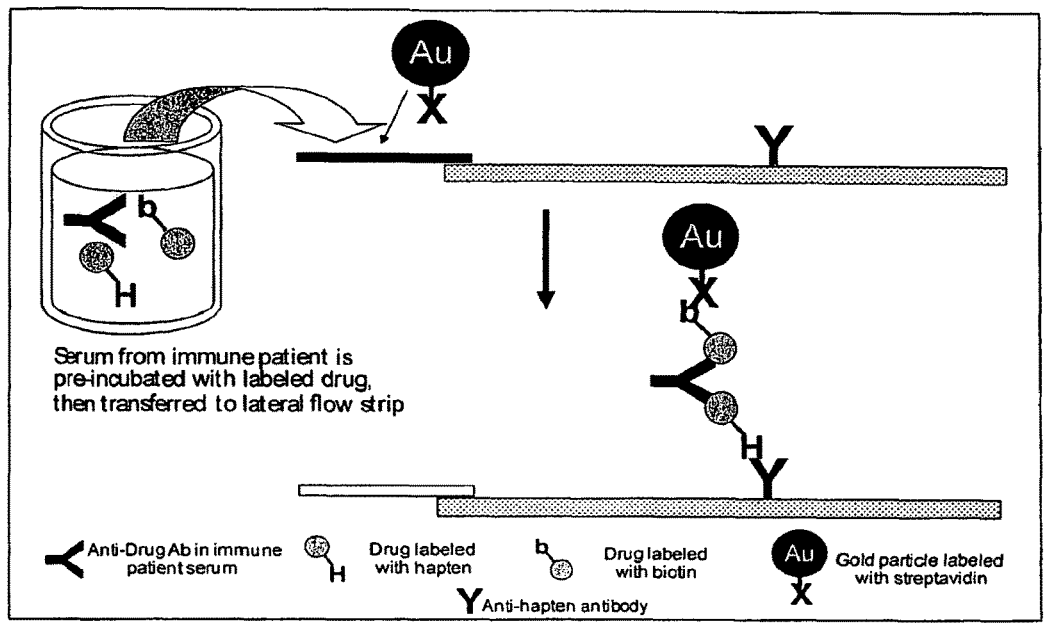
FIG. 1 depicts a configuration of an immunoassay of interest. One binding pair is provided by biotin and streptavidin. The gold particle is the reporter. For the second binding pair, the hapten can be any antigenic molecule while the other member of the binding pair is an antibody to that antigenic molecule which is immobilized on the membrane to provide a capture element or capture agent.

The instant invention relates to an immunoassay for detecting anti-drug antibodies (ADA) using, for example, an immunochromatographic assay format. A suitable format for an immunochromatographic assay is a lateral flow assay (LFA). The assay of interest can adopt a variety of configurations, conformations and formats.

For the purposes of the invention, a "tag" is identified as a moiety attached or conjugated to or with a reagent, such as, a drug, using known materials and methods, where the tag itself does not generate a detectable signal. A tag can be connected to another moiety, such as, a binding partner, containing a signal generator such as a label or a reporter. A tag can include a member of a binding pair, such as, an antibody or an antigen-binding portion thereof, an antigen, an avidin/streptavidin/neutravidin, a biotin, an anti-DNP antibody, a DNP, an anti-digoxin antibody, a digoxin, an anti-digoxigenin antibody, a digoxigenin, a hapten, an anti-hapten antibody, a polysaccharide, a polysaccharide-binding moiety, a fluorescein, an anti-fluorescein antibody, a complementary DNA, an RNA etc.

On the other hand, a "label" or a "reporter" is defined as a moiety that generates a detectable signal either directly or indirectly, for example, on addition of a reactant thereto or therewith, such as, an enzyme label which generates a detectable signal with the addition of a suitable co-reactant/substrate, which when acted with or by the enzyme, yields the detectable signal. The label can be detectable per se, such as visually with the unaided eye or using a visualizing device, such as a microscope, a spectrophotometer, a colorimeter and so on. Hence, such a label can include, for example, an enzyme, a ferritin, a fluorescent or colored microparticle/bead or nanoparticle/bead, a colloid metal, including gold and silver colloidal particles, a quantum dot, a magnetic particle, an up-converting phosphorescent particle, an electrochemiluminescent molecule, compounds containing various metals, including, but not limited to, transition metals, such as Sc, Y, Ti, Zr, Hf, V, Nb, Ta, Cr, Mo, W, Mn, Tc, Re, Fe, Ru, Co, Rh, Ir, Ni, Pd, Pt, Cu, Ag, Au, Zn, Cd, Hg and Os; Lanthanide series elements, such as Ce, Pr, Nd, Pm, Sm, Eu, Gd, Tb, Dy, Ho, Er, Tm, Yb and Lu; Actinide series elements, such as, Th, Pa, U, Np, Pu, Am, Cm, Bk, Cf, Es, Fm, Md, No and Lr; and so on.

For the purposes of the invention, drugs and therapeutics, which are considered synonymous, can include pharmacologically active entities containing various additives and substituents included therewith for beneficial properties, such as, added carbohydrate or glycan for prolonged retention time. Such compositions can be identified as composite drugs (considered synonymous with drugs), which include biological macromolecules, such as polypeptides, polynucleotides, polysaccharides, lipids and combinations thereof, conjugates, modified drug molecules and so on, which are combined with other elements to obtain a beneficial pharmaceutic property, such as, extended residence time or reduced immunogenicity. The other element includes, for example, side groups, functional groups, a water-soluble polymer, such as PEG or PEO, a carbohydrate, a glycan and so on. In one aspect, a drug is described as drug of interest (DOI), which is differentiated from a DOI moiety. For the purposes of the invention, a DOI moiety is a drug that is covalently modified to comprise a tag or a label, such as, for example, a DOI which is connected with a hapten would be a DOI moiety. In a related aspect, whether the DOI or DOI moiety is modified, the epitopes recognized by the ADA are still available after modification.

Thus, for the purposes of the invention, a drug or composite drug is a pharmacologic agent or any compound administered to a mammal. Hence, the invention relates, in part, to an assay that detects whether a host has generated an immune response to a drug, which can be manifest as circulating antibody or an antibody in a body liquid that binds the drug. Thus, any compound or composition that generates a humoral response thereto is amenable for testing using the materials and methods taught herein. Examples of such drugs include organic compounds, polypeptides, polynucleotides, lipids, saccharides and combinations thereof. Thus, for example, therapeutic polypeptides and polynucleotides, such as monoclonal antibodies, or antigen-binding portions thereof, and aptamers are examples of such drugs.

Particular examples of drugs that can be a target of the instant assay include polypeptides, polynucleotides, monoclonal antibody-type drugs, many of which are pegylated, that is, are modified to contain one or more PEG moieties, such as antibodies to CD3, CD20, CD25, TNF, CD25, RSV, IgE, EGF-R, VEGF, GP IIb/IIIaR, HER2, CD33, CD52, CD11a, A4-integrin, GCSF and so on; polynucleotide drugs, such as ribozymes, antisense nucleic acids, siRNA, miRNA, RNAi molecules, aptamers, such as Macugen, which is a pegylated polynucleotide which binds VEGF, and so on; and polypeptide drugs, such as insulin, HGH, an interferon, tPA, EPO, a GLP-1, a glucagon, a cytokine, a blood clotting factor; a pathogen epitope; and so on.

The composite drugs can be substituted, conjugated, labeled or tagged, for example, by inclusion of the added element or substituent during the original drug (protein/peptide/polynucleotide/nucleic acid) synthesis, by chemical modification using various commercially available reagents, including homobifunctional, heterobifunctional or multifunctional groups that include, but are not limited to, an amine (or an oxy-amine), an activated ester, an ester, a carboxyl, a carbonyl (an aldehyde or a ketone), a hydroxyl, disulfide, a sulfhydryl, a maleimide, an iodoacetamide or a photoreactive group, among others with or without a spacer or linker molecule in between. Such spacer or linker molecules may include, but not limited to, a short linker with only one atom between the functional group and the drug to be conjugated, or a long linker, such as a polymer (e.g., PEG or PEO polymers with various molecular weights or branched polymers including asymmetrically and symmetrically branched polymers), a protein molecule (e.g., an albumin or immunoglobulin from bovine, rabbit, mouse, rat, goat, sheet, cow, and human sources, etc.), or a polynucleotide (e.g., a DNA, RNA, or an aptamer, etc.) Antibodies are commercially available or can be made practicing materials and methods known in the art. Conjugation materials and methods are commercially available and known in the art.

Also contemplated within the scope of the invention are assays for detecting presence of antibodies to other antigens, introduced antigens, which comprise any entity introduced into a host, such as food antigens or allergens (FA), environmental antigens or allergens (EA) and so on. Hence, anything ingested, as a liquid or a solid, or introduced into a host, for example, by inhalation or transdermally, can generate an immune response thereto, and an assay of interest can be used to detect presence of and levels of antibody to such introduced antigens. Thus, for example, an assay of interest can be used to detect IgE responses to peanut allergens or other nut allergens, bovine milk, gluten, wheat, eggs, spinach, squash and so on. Similarly, an assay of interest can be used to detect presence of IgE to dust, dander, pollen, microbial toxins and so on.

The assays of interest are directed to identify antibody in a host, such as a pet, a domesticated animal, a human and so on. The antibody can be directed to a variety of antigens, such as any entity that is introduced into a host, such as a drug, a prosthesis, a food, a drink, an entity found in the environment, such as dust, pollen and the like, an autologous antigen that generates a pathologic autoantibody, such as antibody directed to myelin found in various neurologic disorders, antibody to nucleic acid, such as those found in lupus erythematosus, and so on. All of those antigens are considered equivalent for the purposes of the instant invention, and mention of one class of antigen can be interpreted to include inclusion of the other classes of antigen in the absence of evidence to the contrary.

An assay of interest can take a number of formats as a goal is to assess the presence of antibody to a particular drug, pharmaceutic, therapeutic regimen and so on in a body of a host already on a treatment regimen or being considered for inclusion in that treatment regimen. Hence, the following embodiments are for exemplification only.

A "cognate tag" is equivalent to a member and is one entity of a binding pair. The other entity of the binding pair also is a cognate tag or member of the binding pair. The two entities can be identified as the first and the second cognate tags, or members, of a binding pair.

A DOI can be modified covalently, tagged, with a molecule that is a member of a first binding pair, such as a hapten (H). That entity can be referred to as a capture drug molecule. The same drug also can be modified covalently, tagged, with a molecule that is a member of a second binding pair, such as a biotin (b). That is referred to as the detector drug molecule. On the other hand, the reversed configuration can also be used. Both drug composite molecules or moieties are allowed to react in liquid phase with any antibody in a patient sample to form mixed bridged complexes wherein each antibody will bind at least one molecule of each type of labeled drug molecule, see FIG. 1. The preincubation step ranges from minutes to hours, preferably until equilibrium conditions are achieved.

The reaction mixture then is added, in the case of an LFA, to a test solid phase, such as a membrane or a strip containing releasable signal-generating particles coated with the other member of the second binding pair dried on an attached pad at one end of the strip. The other member of the second binding pair is attached either directly or indirectly (optionally, through a branched polymer) to a reporter, such as, a signal generating label or a visible label. In the example shown in FIG. 1, gold particles coated with streptavidin or a branched polymer-streptavidin conjugate are used. Downstream on the strip from the attached pads, for accepting sample and containing releasable reagent(s), is a fixed test or capture site, or a reaction zone consisting of the other member of the first binding pair immobilized on the membrane. The immobilized reagent can serve as a capture agent. The capture agent can be a ligand, a member of a binding pair, and so on. In the example shown in FIG. 1, the test zone contains immobilized anti-hapten antibody. The liquid reaction mixture reconstitutes and releases the releasable reagents, such as, the dried gold particles, which migrates with the particles down the length of the membrane by capillary action to the test zone.

In the example shown in FIG. 1, the anti-hapten antibodies in the test zone bind the hapten attached to the drug molecule that forms a mixed bridge complex with antibody and the biotinylated drug molecule. The streptavidin-coated gold particles or streptavidin-branched polymer conjugate-coated gold particles then bind to the biotin linked to one of the two drug molecules of the bridge complex. The result is a visible red line formed at the test zone or capture site. The intensity of that line is directly proportional to the level of antibody in the test sample and can be measured visually with the unaided eye or by an appropriate reader or reading device. The reader is configured to provide quantitative, semi-quantitative or qualitative (i.e., yes or no) test results. The comparison of the test line signal to a fixed negative cut-off (NCO) signal or a floating/dynamic cut-off point allows determining if the experimental result is positive or negative relative to background, a negative control or other baseline metric or statistic. Alternatively, a derived and stored standard curve enables the conversion or correlation of the reaction zone line intensity on the test strip to an ADA concentration value for the test sample.

The sample containing an antibody can be allowed to react with the labeled antigens or reagents, such as, a labeled drug moiety, a tagged drug moiety and so on, to equilibrium in a preincubation step, followed by measuring the formation of bridge complexes, such as a drug-ADA-drug complex, without any sample dilution and washing steps. That format can, therefore, detect both low and high affinity, as well as low and high avidity antibodies.

Figure 2:
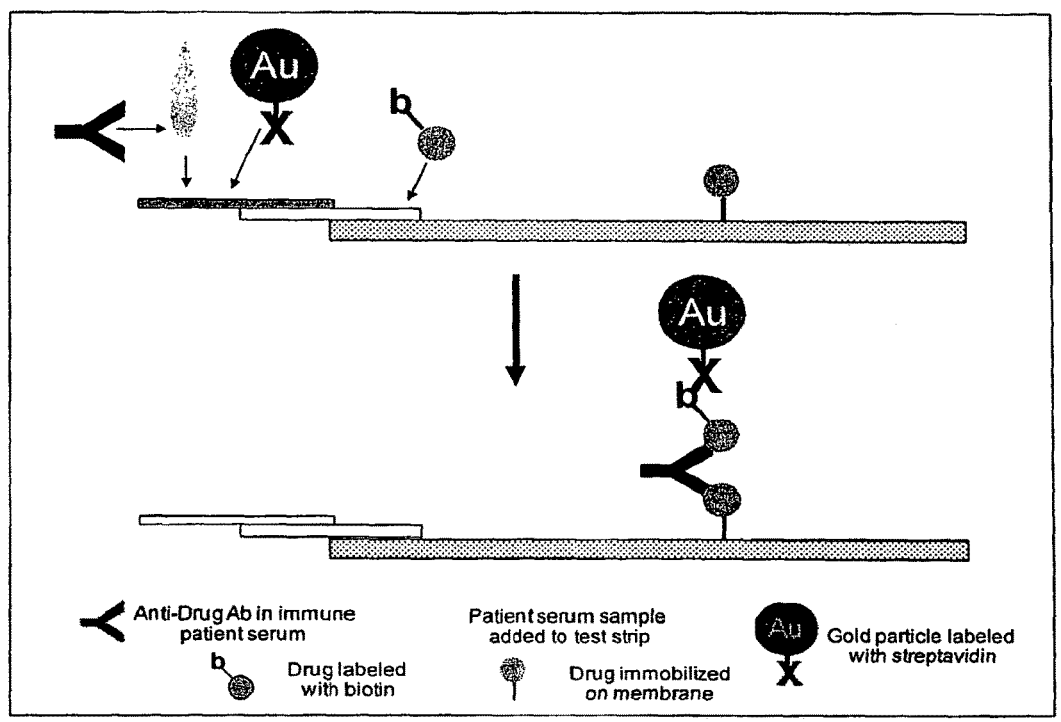
FIG. 2 depicts another configuration of an immunoassay of interest. The drop depicts a liquid sample. The CSP is depicted in the side view as the stippled rectangle. The white and dark gray structures to the left depict plural pads containing LFA reagents and intended to receive the sample.

In another LFA format, a test solid phase, such as a strip or membrane, is used wherein the drug or composite drug is immobilized at the test zone or capture site at a distal area of the membrane either by direct coating or by indirect means. At the other end of the test strip, releasable drug or composite drug linked to a member of a first binding pair, such as biotin (b), is releasably dried, for example, on a second solid phase in fluid communication with the test strip, such as, an attached pad. Another pad in fluid communication with the test strip can hold releasable signal-generating particles coated with the other member of the first binding pair. As depicted in FIG. 2, the streptavidin-coated gold particles or streptavidin-branched polymer conjugate-coated gold particles serve as reporter.

The test is initiated by adding a patient sample, such as a liquid sample, such as serum, blood, plasma, saliva, urine, tears, nasal fluid, and other body fluid, which may or may not be diluted or thinned with a suitable diluent, such as a saline or a buffer, tissue culture medium or wash that carried a tissue, and so on, suspected of containing antibody or known to contain antibody, to a pad attached to a test strip. The serum reconstitutes and releases the releasably dried reagents, such as, gold particles and the biotinylated drug, then migrates along with the particles and the biotinylated drug down the length of the membrane by, for example, capillary action, to the test zone.

The drug immobilized at the test zone or capture site will form a bridge complex by attaching to one binding site of the antibody from the host serum as it flows by, while the biotinylated drug released from the pads will attach to the other binding site or sites (in the case of IgM or IgA) of the antibody to form a bridge structure. The streptavidin-coated gold particles or streptavidin-branched polymer conjugate-coated gold particles then bind to the biotin attached in the captured bridge complex. The result is a visible red line formed at the test zone. The comparison of the intensity of the test line signal to a fixed negative cut-off (NCO) signal or a floating/dynamic cut-off point enables determining if the experimental result was positive or negative. Alternatively, a derived and stored standard curve also enables the conversion of the line intensity on the test strip to an antibody concentration value for the test sample.

In a similar fashion, an ELISA microplate or a bead-based assay can be prepared as above for LFA's, except symmetrical or asymmetrically branched polymers are used to enhance assay sensitivity and to reduce false positive responses. The first and second binding pairs may be reversed for those assays to match different reporter/signal generation systems. For example, avidin/streptavidin or avidin/streptavidin-branched polymer conjugate-coated ELISA plate or beads can be used as capture agent to bind biotinylated drug, while the drug can be directly or indirectly (e.g., through a binding pair bridge, such as, hapten and anti-hapten binding pairs, wherein the hapten can be, for example, a DNP, digoxigenin, digoxin, fluorescein, thyroxine, THC, morphine, amphetamine, heroin, barbiturates etc.) linked to a reporter molecule such as enzymes and/or fluorophores, to form the detector reagent for the detection of antibody. In another embodiment, the biotin-drug can be either pre-coated on the plate or bead as the capture agent, antibody and the detector drug reagent(s) sequentially added, or the biotin-drug can be pre-incubated with antibody and detector drug reagent, and then added to the avidin/streptavidin-coated plate or bead, followed by detection with a reader.

Any body fluid known to contain antibody can be used as a liquid sample in an instant assay. Suitable samples are serum, saliva, tears, urine, nasal fluid, but any liquid sample from a body source known to contain antibody can be used. In some situations, the sample may need to be diluted with a suitable physiologic buffer or saline, such as a sample of a serous secretion from a mucous membrane. Also, a tissue can be macerated or triturated and so on in a suitable liquid medium. The tissue or tissue pieces can be incubated in the medium. The medium is then used as the liquid sample of interest.

A "reader" or "reading device" is a device that provides the ability or capability to detect and to measure a signal, such as fluorescence, light, a color, radioactivity and so on. A reader can comprise a sensing component for detecting a signal, such as a camera, a photomultiplier tube, a scanner, and so on. The reader can contain components, which can be controlled by a processor, computer and so on to manipulate the various components, including the sensing component, the sample or a carrier or holder, of holding device, of one or more samples to enable detecting a plurality of sites or samples at one time or consecutively in a defined order. The reader can be configured as a component of a robotic system that introduces an article of manufacture that carries the sample, or the holder or carrier, into the reading device, and then removes the article of manufacture when the detecting is completed. Spectrophotometers, luminometers, liquid scintillation counters, microtiter plate readers and so on are examples of readers or reading devices. Suitable sample containers or vessels, or carriers or holders of same are used in each, such as, test tubes, scintillation vials, tissue culture devices, such as, microtiter plates, and so on. The instant invention can be applied to identifying antibody or immunoglobulin; or for detecting immunoglobulin (Ig) isotype, class, subclass and so on of specific antibodies expressed by a host animal or a human patient as an immune response to, for example, a food, an environmental antigen a drug or other antigen using an assay of interest, such as a lateral flow assay format. Because some of the assays of interest do not require one or more washings and/or a sample dilution step, the assays are capable of detecting antibodies with a variety of affinities and avidities.

In one embodiment, lateral flow is achieved using at least one strip (or pad) immunochromatographic solid phase. Such a device may comprise at least two components, a proximal solid phase, such as a pad, for loading the sample, and a separate distal solid phase, such as a strip or membrane, for example, in fluid communication with the proximal solid phase, which contains the capture agent in a test or capture zone. In one aspect, the solid phase will contain a third solid phase, such as another pad, where the third solid phase may contain one or more releasably immobilized reagents, such as, a DOI moiety, for example, which third solid phase is in fluid communication with the first and second solid phases. Methods as described herein may use one or more of such solid phases to practice the invention as disclosed, including that such solid phase or solid phases may be contained in a holding device or holder (e.g., but not limited to a plate, a tray, a platform, or combination thereof, where such plate, tray, platform, a dedicated enclosure or combination thereof is adapted to accommodate one or more of the solid phases). In one aspect, at least one strip or pad containing immunochromatographic solid phase is contained in a multi-strip/multi-pad/multi-test immunochromatographic device.

Thus, for example, an anti-hapten antibody can be immobilized as a capture agent or ligand in the test zone on one end along the long axis of a membrane of a lateral flow strip. In a vessel separate from the lateral flow device, the patient sample is allowed to react for a sufficient amount of time at an appropriate temperature with the antigen/drug which has been conjugated to a hapten/tag. During the incubation period the specific antibodies will form an immune complex with the tagged antigen/drug.

An aliquot of the reaction mixture is then added to a test strip which contains at one end, a pad or a series of pads that, for example, serve to receive a sample or to contain releasable reagents, such as, a detector anti-Ig class antibody conjugated with one member of a second binding pair (e.g., biotin) and a releasable signal-generating particle or label conjugated to the other member of the second binding pair (e.g., streptavidin). One of the pads can be dedicated to receiving the sample. Another of the pads can be used to retain excess fluids. The pads can be in communication, directly or indirectly, with the membrane, paper, or surface on which the assay occurs. Movement of solutes (i.e., ADAs and other antibodies) is accomplished by percolation of a mobile phase which is in fluid communication with the pads or strips. As used herein, a mobile phase is a fluid that carries a mixture of substances in a sample through an adsorptive material. For example, where a sample is diluted in a physiological buffer (e.g., PBS), the buffer serves as a mobile phase.

The aliquot of the reaction mixture is added directly onto the pad(s) so that the sample reconstitutes and releases the tagged anti-Ig class antibody and the signal-generating particles or labels to migrate via capillary action along the long axis of the membrane to the reaction test zone or capture site at the distal portion of the test strip where a test control zone, for control reactions, is located. The specific reactive antibody complexed with the hapten-labeled antigen in the sample will be captured by the anti-hapten antibody immobilized at the test zone. The labeled anti-Ig class antibodies will then react with the captured complexes that contain the specific isotype or class of Ig and if so, will be immobilized at the test zone. The captured anti-Ig class antibodies will then react with the reporter or labeled particles via the interaction of the second binding pair, creating a detectable signal at the test zone. A detectable signal indicates that the specific immune response expressed by the host animal or human patient belongs to the Ig class being tested.

An assay control zone will be positioned downstream from the test zone and shall be comprised of immobilized, for example, non-specific Ig class molecules or an immobilized antibody that is specific to the Ig class being tested to provide an indication of an operable assay, that is, a positive control. The generation of signal at the control zone confirms that the assay validly detects the specific class of interest.

An Ig class or isotype can be any one of an IgG, an IgM, an IgA, an IgE or an IgD (FIGS. 19-22). Also, an Ig subclass can be detected, such as, an IgG1, IgG2 and so on. Moreover, the type of antibody can be detected, such as, whether the antibody comprises a kappa or a lambda chain. The reagents, that is, antibody, for conducting such determinations are available commercially or can be made practicing materials and methods known in the art.

Figure 23:
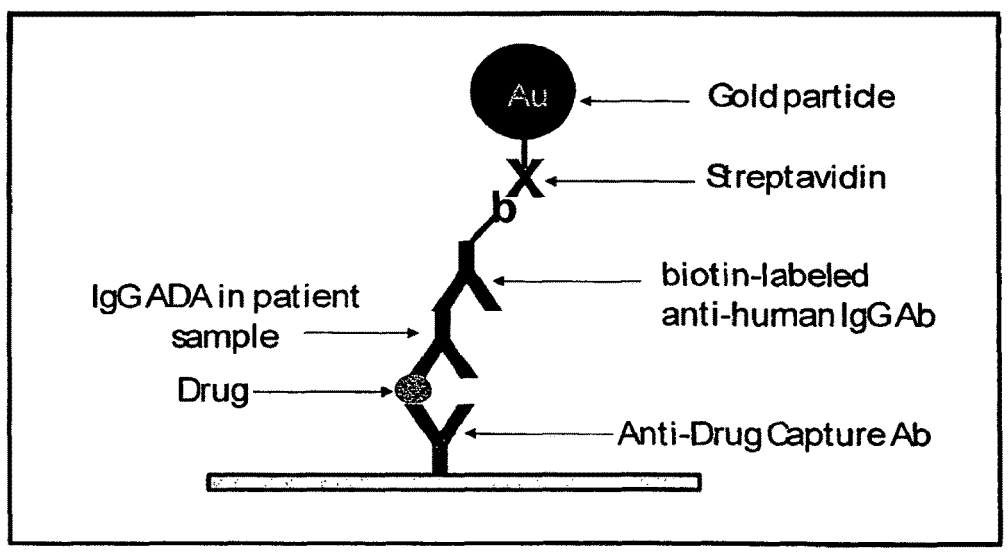
FIG. 23 shows an alternative reaction schematic for an LFA for the identification of Ig isotypes and subclasses where the drug is not tagged or labeled.

Another design for such assays uses an antibody specific for the antigen, which antibody is immobilized as a capture agent in the test or capture zone. In that case, the antigen used in the test generally will not be tagged or labeled. The Ig-specific antibody (detector) is then tagged with a member of a binding pair and the signal producing particle is labeled with the other member of the binding pair. As an example, FIG. 23 shows the use of biotin/streptavidin as the binding pair.

Figure 24:
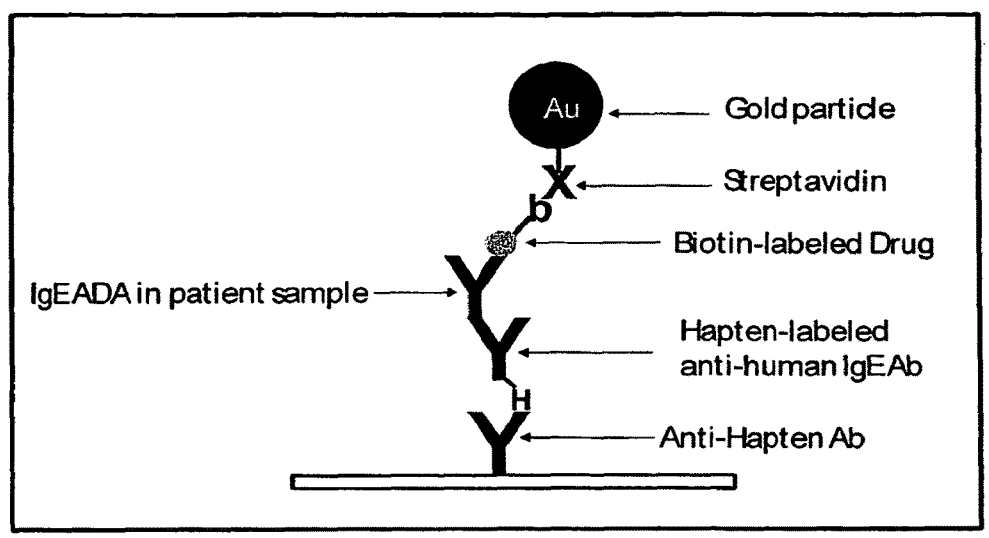
FIG. 24 shows an alternative reaction schematic for an LFA for the identification of IgE and other isotypes or subclasses of ADAs.

Another design for an Ig isotype assay is as follows (FIG. 24): for example, an anti-IgE is tagged or conjugated with a member (e.g., a hapten) of a first binding pair as a capture reagent, while the drug is linked or tagged with a member (e.g., biotin) of a second binding pair as a detector reagent. The solid phase can be coated with, in the context of this exemplification, an antibody, such as, an anti-hapten. The capture agent, a ligand, in the target or assay zone can either be pre-coated on the solid phase followed by sequential binding of any IgE in the host sample, and the detector reagent; or pre-incubated with any IgE from a host sample and the detector reagent, followed by the addition of such mixtures to the solid phase. An avidin/streptavidin-branched polymer-conjugate or an avidin/streptavidin reporter or label can be used as the reporter or signal generator which either can be read by eye or with a reader. Alternatively, the avidin/streptavidin-coated solid phase can be used as a capture surface element, to which is added sequentially biotinylated anti-IgE antibodies, any IgE from the host sample, and a hapten-tagged drug, or to which can be added pre-incubated complexes comprising of the biotinylated anti-IgE, any IgE from the host sample, and the hapten-tagged drug. Either option is followed, for example, by the addition of an anti-hapten or an anti-hapten-branched polymer which is conjugated to a reporter or label, to serve as a reporter or a signal generator.

The platform technology described for the LFA of the instant invention, in so far as the optional use of a branched polymer as described in the preceding paragraphs is concerned, can also be extended to other formats such as ELISA, microbead/particle and nanobead/particle assays, for example. ELISA can employ a variety of configurations and formats, such as, a double antigen bridge format. The ELISA can be practiced using any of a variety of solid phases, such as, a dipstick, a bead, a membrane, a tissue culture substratum, such as, a microtiter substratum, and so on. In that case, the drug either can be coated on a solid phase directly or indirectly, for example, through a binding pair, such as biotin and streptavidin/avidin/neutravidin binding pairs, followed by the addition of a sample and directly or indirectly labeled drug. Alternatively, a tagged drug (e.g., tagged with a member of a binding pair, such as, a biotin), antibody/host sample, and a directly or indirectly labeled drug (e.g., a drug directly or indirectly (e.g., through a hapten and anti-hapten binding pairs) labeled with an enzyme or, for example, a fluorescence moiety) can be preincubated for a period of time, prior to the exposure of such a mixture to a solid phase. If a member of a binding pair is used, the solid phase can comprise the other member of the binding pair, such as, an avidin/streptavidin, an anti-hapten antibody including, but not limited to, anti-DNP antibody, an anti-digoxin antibody, an anti-digoxigenin antibody, an anti-fluorescein antibody, an anti-thyroxine (T4) antibody, any anti-drug of abuse antibody (e.g., anti-morphine, anti-barbiturates, anti-THC, anti-heroin, anti-amphetamine, etc.), an anti-food allergen antigen or any anti-hapten antibody to serve, for example, as a capture agent. Once a binding pair of the capture portion is selected, a different binding pair can be used for the detector portion, particularly for the indirectly linked label, to avoid non-specific or false positive binding. In those cases, the use of a branched polymer linker as part of the reporter moiety attached to the detector or as part of the tag on the capture is applicable and can improve the sensitivity of those assays.

In a similar manner of using branched polymers, microbead/particle or nanobead/particles also can be coated with drug molecules directly or indirectly (through a binding pair), followed by the addition of a sample and labeled drug. The formation of such drug-ADA-drug complexes can then be detected, for example, with a suitable device, for example, a Luminex reader. A tagged drug (e.g., tagged with biotin or hapten), ADA and a labeled drug (e.g., direct labels such as enzyme-labeled or fluorescence-labeled drug) can be preincubated for a period of time, prior to the addition of such mixtures onto, for example, an avidin/streptavidin, or an anti-hapten-coated microbead/particle or nanobead/particle for the detection of antibody. Again, once a binding pair of the capture portion is selected, a different binding pair will need to be used for the detector portion, particularly for the indirectly linked label, to avoid non-specific or false positive binding.

Another objective of the invention is to use an LFA, ELISA or a bead assay platform for detecting antibodies to drug substituents, such as, a charged group, an ester group, a glycan, a carbohydrate, a substituent, a synthetic polymer, such as, PEG or PEO, and so on. Since many biological drugs, with increased in vivo efficacy, are conjugated or covalently linked with one or more substituents, such as, a water-soluble polymer, such as, a PEG or a PEO, it can also be important to develop assays for the detection of antibodies to such substituents, such as, anti-PEG or anti-PEO antibodies, as well as antibodies to a combination of the drug and the substituent, that is, for example, an epitope generated by the combination, such as, a site at the juncture where the substituent is attached to the drug or an epitope generated by the folding of the substituent on the drug surface.

Hence, for example, if a lateral flow assay format is used, a PEG or PEO polymer is tagged with a member (e.g., a hapten) of a first binding pair to form a capture reagent, while another PEG or PEO polymer is linked with a member (e.g., biotin) of a second binding pair to form a detector reagent. A solid phase can be coated with a ligand, in the example presented herein, an anti-hapten. The capture reagent either can be pre-coated on the solid phase followed by sequential binding of any anti-PEG/PEO antibodies in the host sample and the detector reagent, or, alternatively, the capture reagent can be pre-incubated with any anti-PEG antibodies in the host sample and the detector reagent, followed by the addition of such a mixture to the solid phase to conduct the assay. On addition of, in the example herein, avidin/streptavidin or avidin/streptavidin-branched polymer labeled with a reporter or a label, the signal can either be read by eye or with a reader. If an ELISA or a bead assay format is used, the branched polymer-avidin/streptavidin-coated solid phase can be used as a capture surface element, followed by sequential binding of a biotinylated drug, any anti-PEG antibodies from the host sample and a hapten-tagged drug. Alternatively, pre-incubated complexes comprising the biotinylated drug, any anti-PEG antibodies from the host sample and the hapten-tagged drug can be added to the capture surface prior to the addition of the anti-hapten conjugated reporters or labels or anti-hapten-branched polymer conjugated reporters or labels. In addition, directly labeled drugs without the need of the second binding pair (e.g., hapten and anti-hapten) also may be utilized.

In the case of any one substituent, it is known that a substituent can comprise a genus comprising a plurality of species. For example, a hydrocarbon substituent can have different sized by the incremental addition of a carbon atom, can be linear or can be branched, for example. Accordingly, suitable detectors, such as antibodies for the target are employed to ensure the desired or all forms of a genus of substituent are detected.

In some cases, a polymer, for example, a PEG or a PEO, can be used for an assay that employs a direct drug-label/reporter conjugate, to enhance assay performance. Thus, a PEG or a PEO can be used as a capture element or a detector element. The molecular weight of the PEG/PEO polymers can range from about 500 to about 1,000,000; from about 2,000 to about 100,000; or from about 10,000 to about 50,000 to detect PEG antibodies.

The assays described here can also utilize branched polymers or dendritic polymers, such as, symmetrical and asymmetrically branched polymers, such as those described in US Pub. Nos. 20060041058, 20080114077 and 20080200562, or other dendrimers or dendritic polymers. The symmetrically branched polymer can include, but are not limited to, star-shaped polymers, comb-shaped polymers, starburst dendrimers, combburst dendrigrafts and hypercombbranched polymers, while the asymmetrically branched polymer can include polylysine dendrimers, randomly branched polymers etc.

According to the present invention, a symmetrically branched polymer is a type of macromolecule in which a number of chains may radiate from a central portion or region, which can be an atom or cluster of atoms, where the chains radiate in a substantially exact correspondence on either side of a dividing line, plane, center or axis. Thus, the chains can be of or about the same length and the branches occur at or about the same sites. The result is an overall symmetry to the configuration, construction and appearance of the overall structure.

In contrast, an asymmetrically branched polymer is a type of macromolecule in which a number of chains may radiate from a central portion or region, which can be an atom or cluster of atoms, or there may be no core or central region, where the chains do not radiate in a substantially exact correspondence on either side of a dividing line, plane, center or axis. Thus, the branch length can vary or be random and the branch sites can vary or be random. Thus, there is no overall symmetry to the molecule at any level, in the shape, constitution or configuration of the asymmetric dendritic polymer.

Normally, the branched polymers or dendritic polymers are constructed of small molecule monomers, such as small hydrocarbons, substituted hydrocarbons, such as an amine and so on. While a branched polymer may be made from an amino acid or a base, nucleoside or nucleotide, the branched polymers or interest are not meant to be biologic informational molecules, such as proteins and nucleic acids. Thus, a branched polymer of interest can be comprised of one amino acid, such as polylysine. Thus, a branched polymer of interest generally is comprised of only a single type of amino acid or a single base, nucleoside or nucleotide.

The utilization of such polymers can further improve assay sensitivity and reduce assay background. That can be important for immunogenicity testing, where the antibody concentrations can be low in host animal and human samples, such as, fluids, such as, urine, saliva, tears, nasal fluid, blood, serum and plasma. The dendritic polymers can serve as intermediates or as a means for attaching or conjugating one component or reagent to another, particularly components or reagents with a recognition or binding ability or function. Thus, for example, a branched polymer can be used to attach a member of a binding pair to a particle, label or reporter.

The various reagents used in the practice of the instant invention generally are commercially available or can be made practicing materials and methods known in the art, such as antibodies, bibulous paper, chemical reagents, dendritic polymers, reporters, nitrocellulose, buffers and so on. The various materials are arranged and configured as taught herein or in the references cited herein, or as known in the art, as a design choice.

Hence, an article of manufacture of interest is one which can be used to practice the method of interest. In the context of an LFA, the article can be configured to permit access of a liquid delivery device to the article so that a sample can be applied to a solid phase or a chromatographic stationary phase (CSP) intended to receive the sample. The article will contain the CSP on which the assay occurs, as well as additional solid phases, for example, carrying the reagents and to accept the sample; as well as capture reagents immobilized at sites on the CSP as taught herein. Another article of manufacture comprises the assay device, and further can include additional assay devices, vials or other containers for one or more reagents, a vessel or vial for a diluent or wash medium, one or more empty vessels for sample treatment prior to testing and so on.

In one embodiment, an LFA device is one including at least one block, wherein the block contains a projection or a depression along the periphery of an upper surface, a lower surface or both, and a first channel therein, where the first channel is configured to accept at least one CSP removably engaged within the first channel. In other embodiments, the block contains 3, 4, 5, 6, 7, 8, 9, 10, 11, 12, 13, 14, 15, 16 or more projections or depressions. The corresponding and complementary projections and depressions are sited on portions to be joined to enable a projection to engage a depression so as to provide a means of securing or joining the two portions. The block can comprise a CSP support structure.

In another aspect, the device includes an adaptor means or portion which is configured to contain at least one second channel of sufficient depth to accommodate the perimeter dimensions of the block, where the block is removably engaged within the second channel. In a related aspect, the adaptor means or portion is configured to engage projections or depressions of the block with corresponding and complementary projections and depression along the periphery of an inner surface of the adaptor means or portion.

In another aspect, the device includes a lid which is releasably attached to the upper surface of the block, where the lid includes at least one opening at one end which is adapted to allow application of a liquid sample to one end of the CSP. In a related aspect, the lid further includes an aperture, such as, a substantially rectangular aperture, separate from the opening for sample application, which aperture is configured to allow an unobstructed view of the reaction zone of the CSP so as to enable detection of any bound reporter in a reaction complex at particular sites on the CSP.

In one aspect, the adaptor means or portion includes one or more compartments segregated by one or more separating structures.

In another aspect, the device includes a reading device, where the adaptor means or portion is removably engaged with a receiving site contained within the reading device.

In another embodiment, an LFA device includes a lid, where the lid includes one or more sleeves on an inner surface; at least one CSP support structure releasably attached to the lid; at least one CSP removably engaged on the CSP support structure; and a base structure, where the base structure is configured to be of sufficient depth to accommodate the CSP support structure, and where the CSP support structure is removably engaged within the base structure.

In one aspect, the CSP support structure is configured to contain at least one channel on a top inner surface adapted to accommodate a CSP therein. In a related aspect, the channel includes an integral tripartite manifold structure, where the tripartite manifold structure includes an inverted substantially cruciate projection at a first end of the manifold structure; a projection in the middle of the manifold structure; and a projection at a second end of the manifold structure. The manifold structure supports the CSP and any other solid phases present, such as pads. In other embodiments, the CSP support structure is presented in different shapes and sizes, can be a single structure that approximates the shape and size of the CSP and so on. The CSP support can be divided, as exemplified, to save on materials, for example. Also, the CSP support structure can vary in width, such as at the sites of additional solid phases. Moreover, the CSP support structure can comprise portions perpendicular thereto to produce a void thereon to frame and to contain a CSP.

In another aspect, the CSP support structure further includes a dowel, where the dowel is configured to secure the lid to the support structure via engaging opposed sleeves in the lid. In a related aspect, the lid includes at least one opening at one end which is adapted to allow the application of a liquid sample to one end of the CSP, and where the lid includes an aperture separate from the opening, which aperture is configured to allow analysis of a reaction complex at a reaction zone of the membrane. In other embodiments, the support structure includes, 2 dowels, 3 dowels, 4, 5, 6, 7, 8, 9, 10, 11, 12, 13, 14, 15, 16 or more dowels.

In one aspect, the lid is transparent. In another aspect, the support structure comprises a plurality of stabilizing projections on a bottom surface.

In a further aspect, the device includes 2 or more CSPs. In a related aspect, the device includes 3 CSPs, 4, 5, 6, 7, 8, 9, 10, 11, 12, 13, 14, 15, 16, 17, 18, 19, 20, 21, 22, 23, 24 CSPs or more.

In another aspect, the device includes 2 or more CSP support structures. In a related aspect, the device includes 3 CSP support structures, 4, 5, 6, 7, 8, 9, 10, 11, 12, 13, 14, 15, 16, 17, 18, 19, 20, 21, 22, 23, 24 CSP support structures or more. The two or more CSP supports can be integrated or joined into a unit to carry corresponding two or more CSPs.

In one aspect, the device includes the suitable number of openings and apertures corresponding to the number of CSPs in the device. In one embodiment, separate openings for sample application minimize sample contamination. Purpose-build designs enable accommodating any number of assays per device as a design choice.

In another aspect, the device includes a reading device, where the base structure is removably engaged with a receiving site contained within said reading device.

As used herein, "chromatographic stationary phase" ("CSP") means the part of the immunochromatographic system though which the mobile phase flows and where distribution of the solutes between the phases occurs. The stationary phase may be a solid or a liquid that is immobilized or adsorbed on a solid. The stationary phase may consist of particles (porous or solid) or a fibrous material (e.g., nitrocellulose, nylon or polyamide, glass fiber, wick, glass micro/nanochannels, plastic micro/nanochannels or paper). The CSP may be presented in a variety of forms, including a planar, thin sheet, such as a paper. A lateral flow assay strip, commonly comprising nitrocellulose, is one example of a CSP.

A "reader," "reading device" or "reading means" is a device that provides the ability to detect and to measure an appropriate signal, such as fluorescence, light, a color, radioactivity and the like with a suitable sensing means, such as a photomultiplier device, a CCD device, a CMOS device and so on. For example, a plate reader is a device that enables the detection and measurement of an appropriate signal such as fluorescence, light, color, radioactivity and the like generated at test zones in the form of dots, spots, lines or other defined geometries or shapes in an organized pattern on a planar surface of a sample carrier, such as a plate, or such signal generated within liquid mixtures in multiple containers arranged in a planar grid in a carrier such as a 96-well microwell plate. The reader can contain processor-controlled means to manipulate the sensing means, the sample or a carrier or holding means of one or more samples to enable detecting a plurality of sites or samples at one time or consecutively in a defined order. Such a reader can use colorimetric, fluorescence, luminescence, electroluminescence, magnetic, electromagnetic, refractive index, light reflection, surface enhanced Raman, radioactive, fluorescence polarization, time resolved fluorescence, UV, etc. measurements. For color based readers, a charge coupled device (CCD) camera, complementary metal oxide semiconductor (CMOS), scanner (i.e., flatbed scanner), or light reflection based image capture devices can be used. For color based readers, a light reflection based reader can be used to generate signals in the assays described herein. In addition, a CCD/CMOS camera or a scanner can be used to generate an image, which can then be processed using a pattern recognition software to generate quantitative or semi-quantitative results. The raw signal/images can also be digitized or stored as an electronic record. Furthermore, the reader can be configured as a component of a robotic system that introduces an article of manufacture that carries the sample, or the carrier, into the reading device, and then removes the article of manufacture when the detecting is completed. Spectrophotometers, luminometers, liquid scintillation counters, microtiter plate readers and so on are examples of readers or reading devices. Suitable carriers are used in each, such as, test tubes, scintillation vials, tissue culture devices, such as, microtiter plates, and on the like, which will be apparent to one of skill in the art.

For the purposes of the invention, LFA devices are disclosed that enable an LFA CSP to be analyzed in a reading device and such reading devices are capable of measuring the test signal on CSPs. Thus, as depicted in some of the figures, microtiter plate readers are designed to read or to detect signal in the individual wells of a standard microplate in which immunoassays are conducted in the individual wells thereof. Hence, a plate reader has a means to accept individual microplates and then a means to read a signal from each of the wells in the plate. The plate reader then provides the measurements from each of the wells for data analysis. In the context of the present invention, the LFA devices enable a multiplicity of LFA CSPs to be analyzed, for example, in a standard microplate reader. Hence, the LFA devices have an overall presentation not dissimilar from a standard microplate device, such as a 96-well ELISA plate, where the interior of the LFA devices is configured to accept and to present to the reader one or more LFA CSPs. The LFA devices can be constructed of any suitable material and can include features as a design choice, as will be apparent to one of skill in the art.

Many current diagnostic assays that employ an immunoassay format are designed to be automated for high through-put. Hence, reagents can be applied to a test device by an automated means, such as a computer-controlled robotic arm; the test device then can be placed, again, for example, by a robotic means, into a detecting means, a reading device or reader, such as a colorimeter, luminometer, a luminescence detecting means, a device based on luminescence can be less complicated than one based on fluorescence because an incident light source is not needed, a time resolved fluorescence detecting means, such as, a liquid scintillation counter, a fluorescence polarization detecting means, a radioactivity detecting means, a fluorescence detecting means, such as a light detector, such as a photomultiplier tube, and so on, where the presence of a suitable reporter is determined; and once completed, the robotic means can move the read test device to a holding or storage area. The results of that determination are digitized and communicated to a data storing means and data processing means for interpretation of the data. Thus, for example, there are a number of ELISA plate readers, luminescence readers and the like which are configured for operation with an article or test device having a plate format that is similar to or is a microtiter plate with, for example, 96 wells, 384 wells and the like, where the assays can be conducted in a well or a sample of a test can be placed in a well.

In another embodiment, a multi-LFA device of interest is analyzed in a dedicated reading device. The form of the multi-LFA device is a design choice.

An LFA of interest can be one which is conducted as a unit assay wherein a CSP to which the sample is applied and on which the assay occurs, is housed in a holding or housing means or device comprising an inert material, such as, a plastic or polymer, configured to include a sample access means and a result detecting means, see for example, WO2006119160. In one embodiment, the result is an LFA device, comprising a "ticket" (a substantially rectangular block, that is one side is longer than the adjacent side) to which the sample is added and the result can be detected, by using, for example, visualizing, reading, scanning and so on means in the reaction zone of the assay strip. The ticket can be configured to run a single assay, with the housing means having the dimensions that approximate or are small than that of a microscope slide. The single ticket can also be configured to run a plurality of assays. The LFA device of the present invention provides support for the membrane and serves as a barrier or protecting means for the membrane on which the assay reaction occurs.

Figure 25:
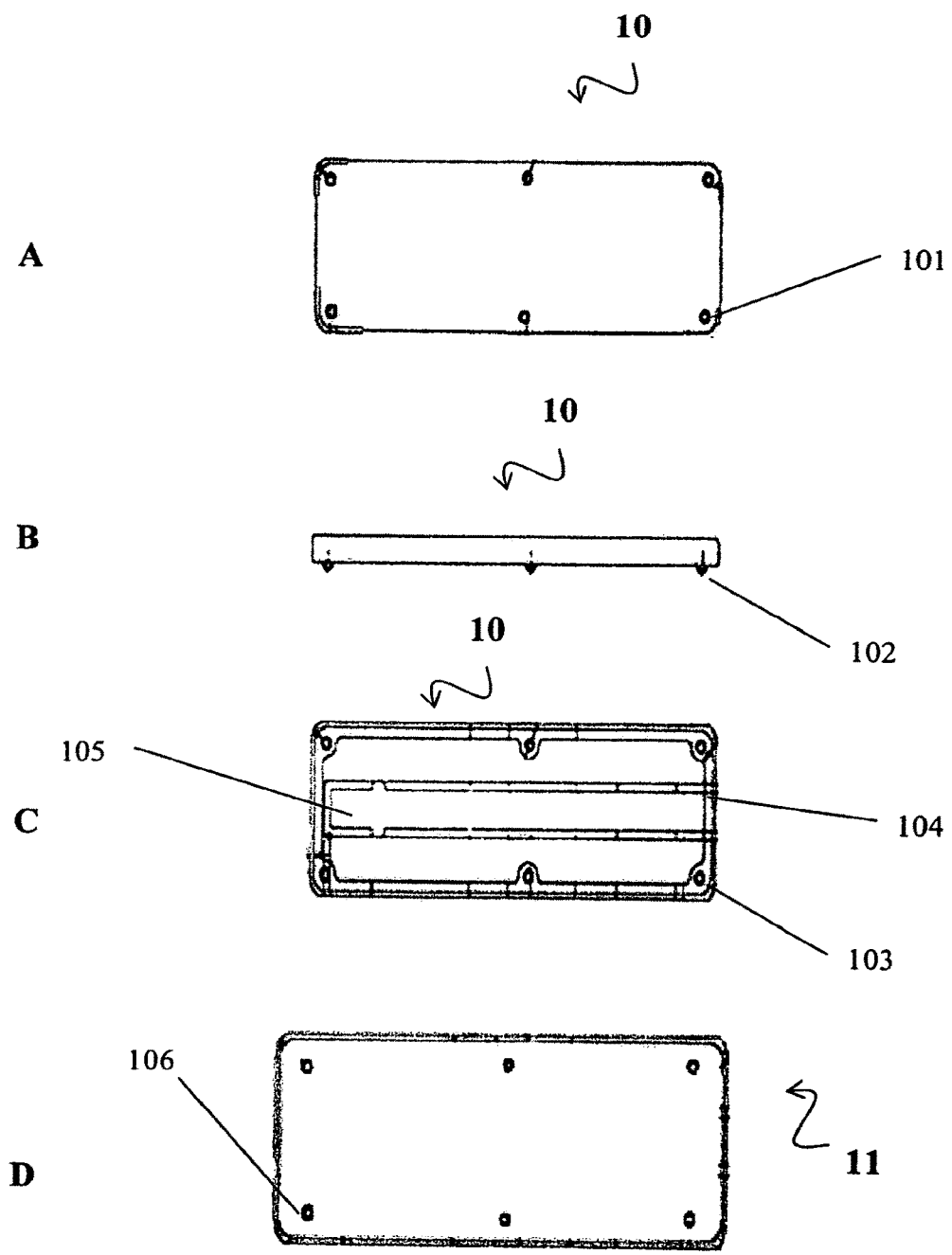
FIG. 25 shows a isometric views of a ticket of one embodiment of an immunochromatographic device. A is an inferior perspective; B is a side view; and C is a superior view enabling a view of the interior of an LFA device of interest. D depicts an optional adaptor means for a ticket.

FIG. 25 depicts views of portions of a ticket 10 (including an adaptor means 11), which is adapted to carry a CSP 109 (see FIG. 27) for conducting an LFA. The top view (A) depicts the inferior surface of the lid of a ticket 10, the surface also contains protrusions 101 depicted as feet 102 in the edge on perspective. Protrusions 101 are depicted as the six sites spaced on the periphery at the corners and midway of the longer sides. The second view (B) depicts a side view of the ticket 10. The ticket includes feet 102. View (B) also can depict an inferior perspective of a lid which engages the CSP support structure. The third view (C) provides a superior vantage depicting the interior of the ticket 10 as well as the superior perimeter thereof. Voids 103 to accept the feet 102 of a lid are depicted as the six sites spaced on the periphery at the corners and midway of the longer sides and in register with the protrusions 102. The protrusions and voids also serve to orient and to affix the various solid phases, such as the CSP and the various pads in place within the ticket. The ticket 10 also contains ridges 104 running parallel to the sides of the longer axis providing a channel 105 for retaining a CSP 109 for an LFA. The fourth view (D) depicts an adapting means 11, which can be the inferior surface of the body of the ticket depicted in (C), to enable the ticket 10 to be read in an existing reader or reading device or to enable stacking the ticket 10 in register, voids or projections 106 in the adaptor means 11 permit corresponding and complementary protrusions or depressions at the inferior surface of the ticket 10 (not shown) to be secured in and to said adaptor means 11. Hence, an existing reading device can be used, so long as an existing sample containing means of the existing reading device is one which can accept a ticket 10, for example, one which approximates the size of a microscope slide.

Figure 26:
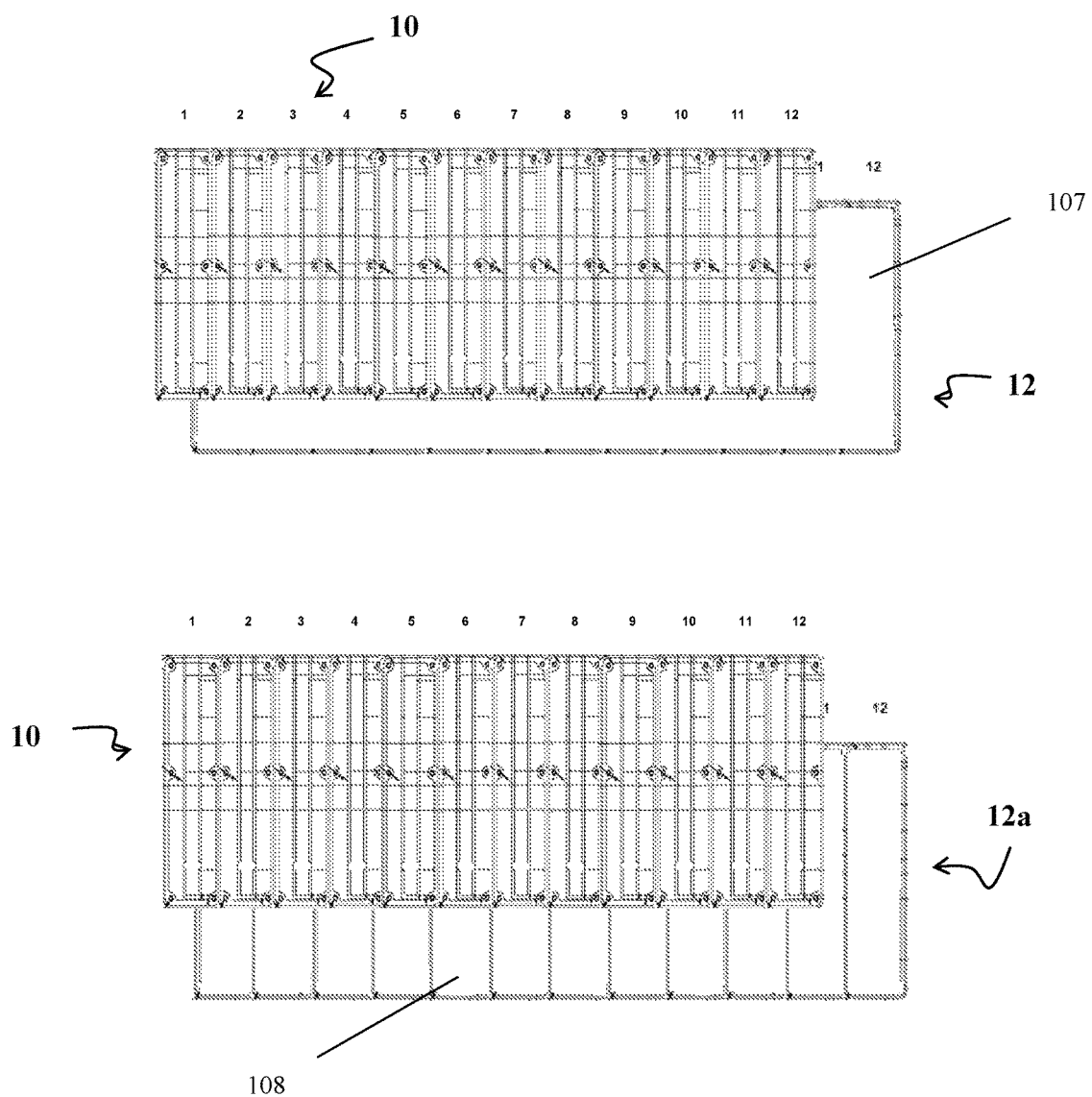
FIG. 26 shows a top view of an adapted arrangement of a plurality of tickets shown in FIG. 1, including an adaptor means for seating the plurality of tickets. Two different adaptor means 12 and 12a are provided.

FIG. 26 depicts the assembly of plural tickets 10 for running plural LFAs. An adapting means 12,12a can be configured to approximate the shape and size of the sample containing means of an existing reading device, and, the adaptor means 12,12a is modified to accept one or more tickets 10. Hence, the adaptor means 12 provides a support to carry the one or more tickets 10 where the adaptor means 12 affixes and removably secures the tickets 10. As shown in the figure, the adaptor means 12 may be configured without separators 107 or the adaptor means 12a may be configured to contain one or more separators 108. The adaptor means 11,12,12a may be made from any of a variety of known materials, such as a plastic, such as a polypropylene, polystyrene, acrylonitrile butadiene styrenes and the like. The adaptor means 11,12,12a can be molded to provide sites, such as voids or feet 106 for securing the ticket components or to enable the stacking of adaptors. Alternatively, the adaptor means 11,12,12a may comprise a securing means. The securing means may be a locking means to secure the tickets 10 in place. Such securing means may be, for example, a movable bar, a cover and the like that secures a ticket 10 in place. For example, the adaptor means 11,12,12a may comprise a pair of ridges running along the long axis of the adapting means 11,12,12a that frame the longer edges of the ticket 10. The pair of ridges thus produces a shallow channel on the adapting means 11,12,12a. An adapting means 11,12,12a may comprise flexible tabs or projections, as securing means, which may be evenly spaced about the periphery, attached to the adaptor means 11,12,12a that produce an opening slightly small than the lower surface area of a ticket 10. The ticket 10 may be placed into the channel by a twisting motion during placement, by inserting the ticket 10 at an angle, using pressure to force a reversible expansion of the adaptor means 11,12,12a to then accept the ticket 10 and so on. In such an example, once in place, the securing means returns to the original orientation, now resting on or above the ticket 10, thereby securing the ticket 10 in place. The actual configuration of the adapting means 11,12,12a is a design choice and would be readily apparent to one of skill in the art.

Figure 27:
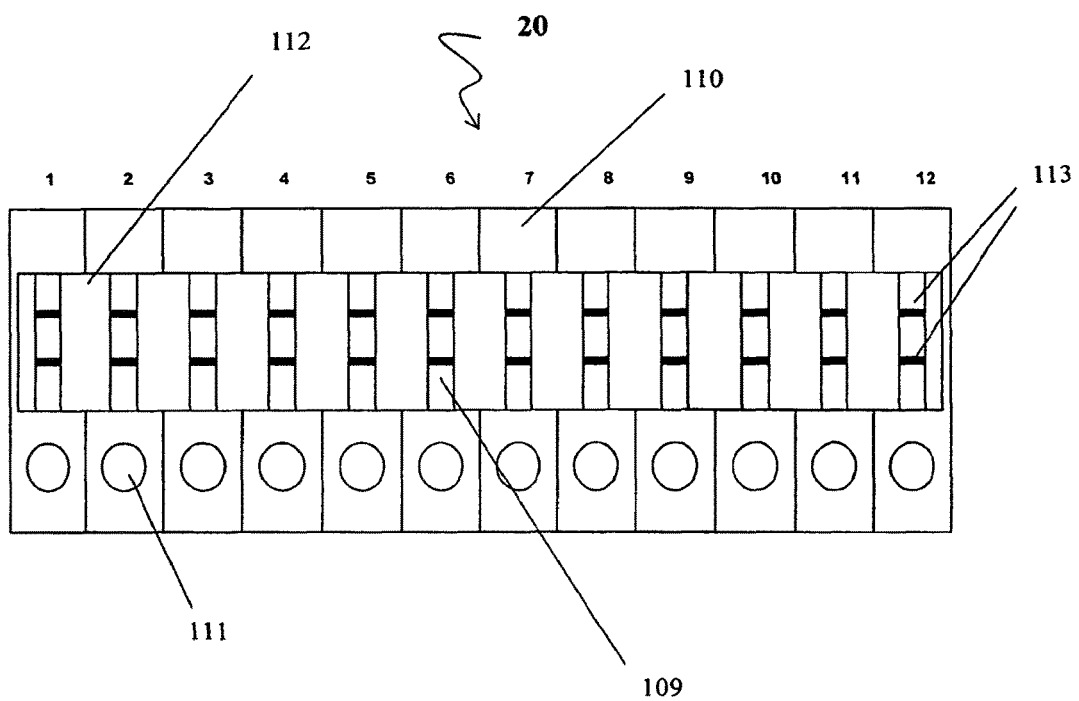
FIG. 27 shows a top view of a lid of another embodiment of an immunochromatographic device which secures a plurality of CSPs in parallel.

FIG. 27 depicts a plurality of CSPs 109 in parallel secured in place with a lid 110 in another embodiment of an immunochromatographic device 20. The lid 110 affixes and secures the ends of the CSPs 109. The lid 110 contains ovals 111, where sample is applied to the CSPs 109 and a central open rectangular area 112, where the reaction zones 113 (shown as two dark bars) of each of the CSPs 109, can be visualized, scanned, read and the like.

Figure 28:
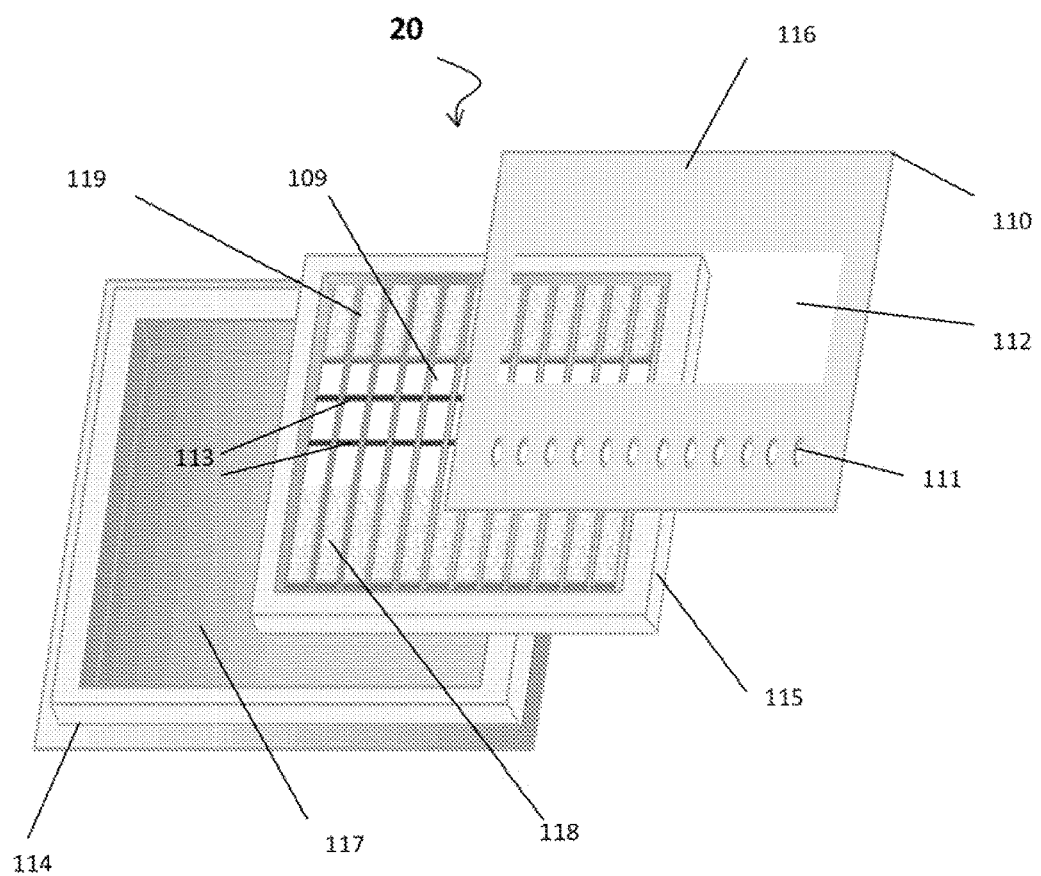
FIG. 28 shows an exploded view of an immunochromatographic device, illustrating the three main components thereof.

FIG. 28 depicts an immunochromatographic device 20 as comprising three main parts 110,114,115. The inferior surface comprises a housing floor 114 with a central void 117 to accept the CSP support structure 115 which houses the plural CSPs 109 for conducting LFAs. The CSPs 109 are aligned in parallel in the CSP support structure 115, which will sit in the housing floor 114. The reaction zone 113 of the strips 109 is depicted with the two bars on each CSP 109. Superior and to the right is the lid 110 which also maintains the CSPs 109 in place and provides a protective barrier for a CSP 109. The lid 110 contains plural ovals 111 through which the samples are applied to the CSPs 109, and a void 112, which when the lid 110 is seated on the CSP supporting structure 115, will provide visual or detection access to the reaction zone 113 on the CSPs 109. Also depicted are pads 118,119 on either side of the CSP, 118 can be a sample receiving pad and 119 can be a reserve pad for wicking fluids and excess reagents. The lid surface 116 can be translucent, opaque or transparent.

Figure 29:
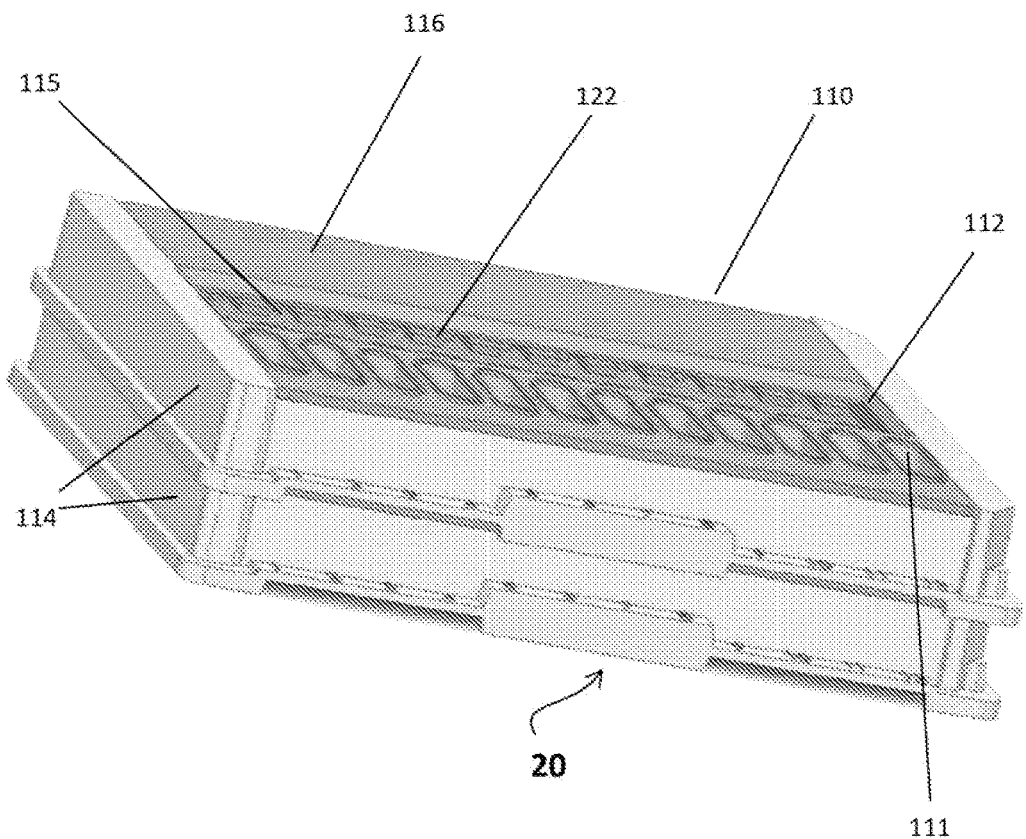
FIG. 29 shows a perspective view of two immunochromatographic devices stacked in register.

FIG. 29 depicts two immunochromatographic devices 20, stacked in register. The presentation of the devices 20 approximates that of a standard 96-well microtiter plate and is intended for use in a reader of same. Sample access is provided through the oval ports 111 which are visible in the Figure. The rectangular void 112 is visible, adjacent to the row of oval ports 111, revealing the CSPs 109 within the device 20. Parts of the manifold structure 122 are also shown.

Figure 30:
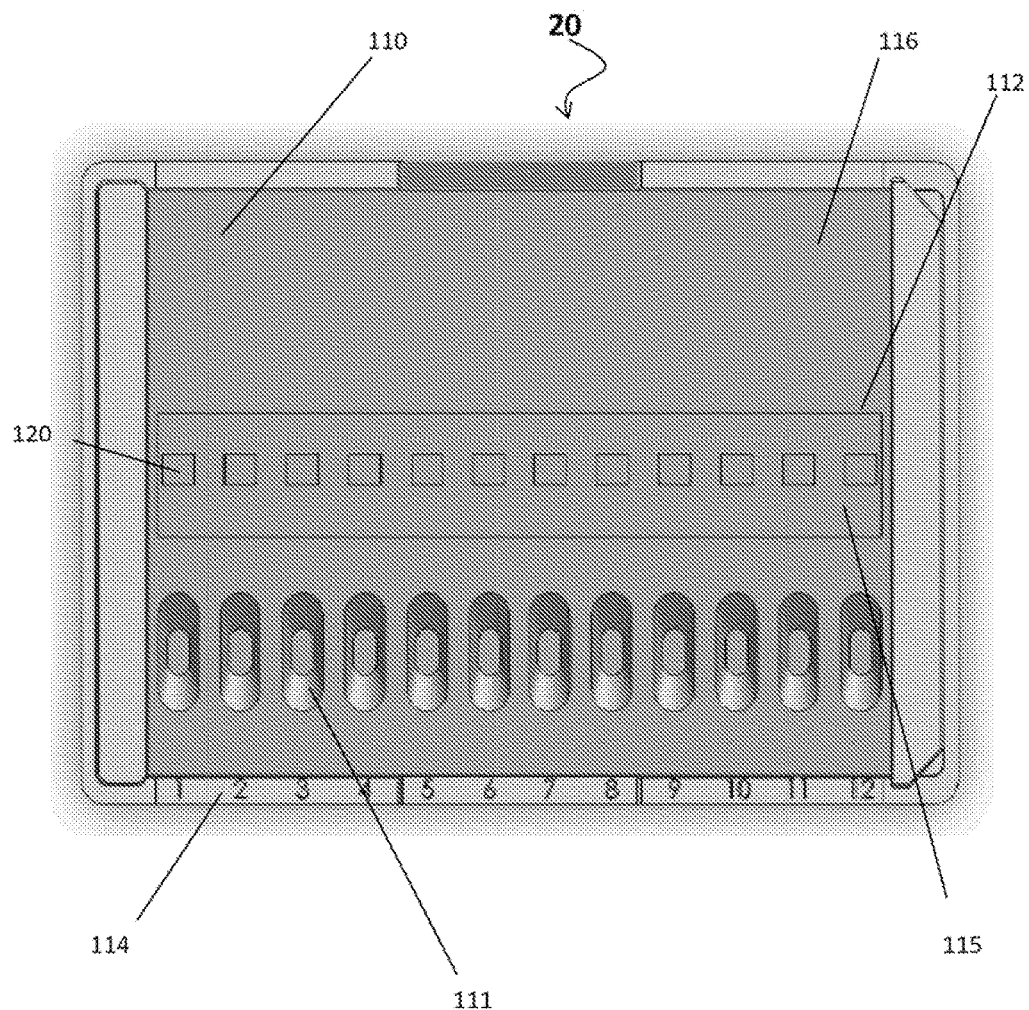
FIG. 30 shows a top view of an immunochromatographic device.

FIG. 30 depicts a superior view of the immunochromatographic device 20 from above. The tapering ovoid sample accesses 111 are provided, and the lighter colored ovoid shape within each access position represents a pad 118 (see FIG. 28) for receiving the sample, which pad 118 is in fluid communication with the CSP 109 on which the reaction occurs. The aperture 112 above the capture sites or test zones 120 enables detecting the reaction (i.e., a "window") revealing the reaction zones 113 (see FIG. 28) of the membranes within 109.

Figure 31:
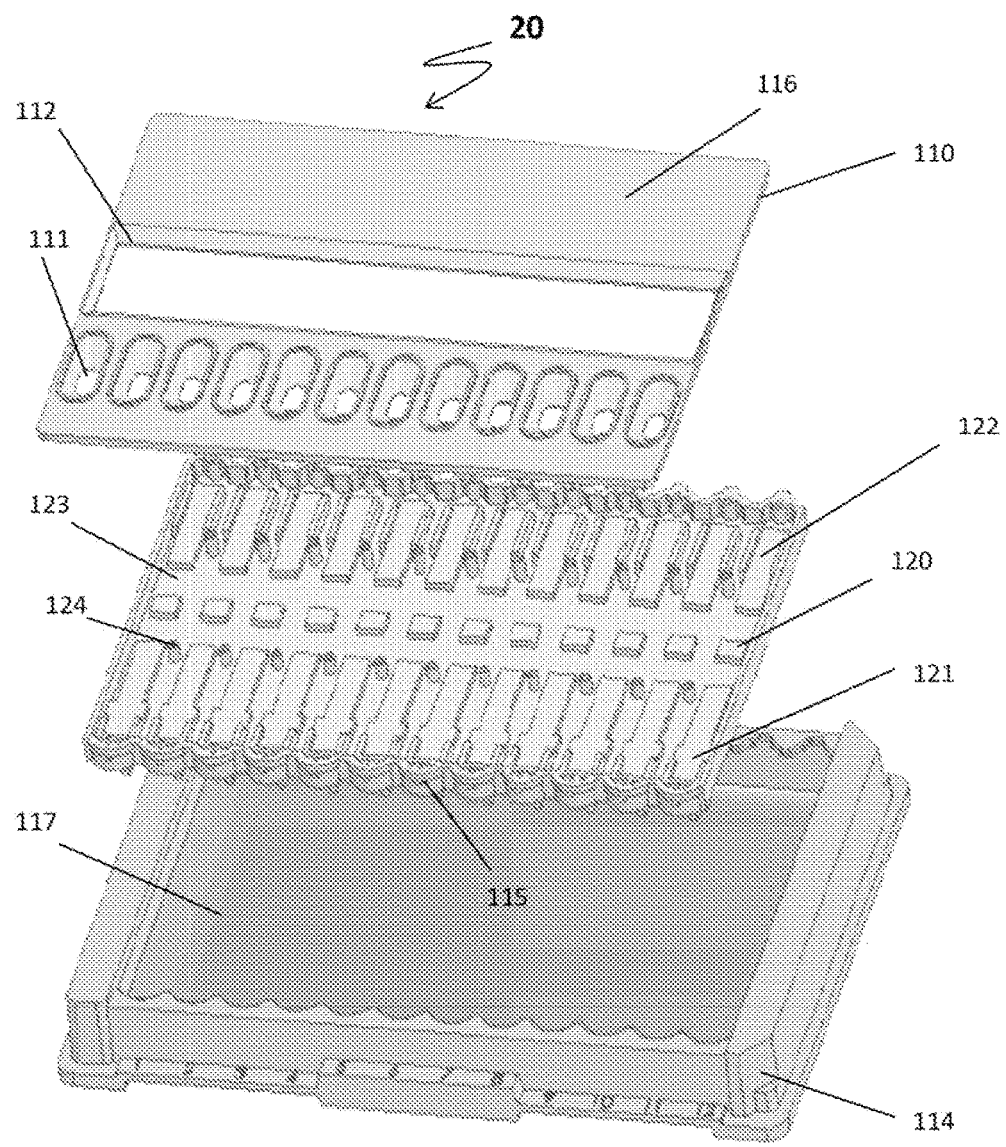
FIG. 31 shows an exploded view of an immunochromatographic device adapted for an existing plate reader or for a dedicated reader wherein the assay carrier is configured in the form of a multiwell tissue culture plate.

FIG. 31 presents an exploded view of an immunochromatographic device 20 configured for compatibility in a plate reader. The lid 110 and surface 116 make up the superior structure of the three structures 110,114,115 providing the sample access positions 111 and the aperture 112. The CSP support structure 115 depicts twelve sets of tripartite manifold structures 120,121,122 on which the CSPs 109 rest, each tripartite structure 120,121,122 comprising an inverted cruciate form 121, the cross form 121 is intended to support the various pads 118 (see FIG. 28) carrying reagents for the LFA as well as the sample accepting pad. The middle portion of the tripartite structure 120,121,122 the manifold strip holder 120, is a smaller central structure to support the CSP 109 at the site of the aperture 112, to ensure stability of the CSP 109 for detecting or reading. The last portion of the tripartite structure 122 is another form for supporting the CSP 109 and/or pad 119, for example, to collect fluids and excess reagents. The CSP supporting structure 115 provides a well 123 for receiving any overflow fluids. A series of pins or dowels 124 are distributed over the structure 115 intended to be housed in receiving voids present at the lower surface of the lid 110 to provide alignment of the two portions 110,115 of the device 20. The third structure 114 is the base or frame providing a means of support for the CSP support structure 115 of the device 20, and is shaped and configured to enable stacking of individual CSP support structures 115. As provided above, an LFA commonly comprises a CSP in which the assay occurs by the capillary flow of fluid there through one or more pads. The CSP generally is a planar structure, such as, a membrane, a paper and the like which is conducive to capillary flow of a fluid. Nitrocellulose, nylon or polyamide, paper, glass fiber and so on are examples of such a membrane. The pads can vary in number and can comprise any of a variety of membrane or paper type products, which can be made from a variety of materials. The one or more pads can be used to accept the sample, to carry reagents dried thereon and therein or to accept excess fluids, for example. The pads may be in fluid communication with the assay CSP. The pads and CSP may be supported by a rigid backing material, such as, a plastic or other polymer, to generate an article of manufacture, an assay or test strip. The assay CSP configuration contributes to ensuring the components are in efficient fluid communication. Such a CSP is then placed onto support 115. Alternatively, base structure 114 and CSP supporting structure 115 can be combined into a single piece.

Figure 32:
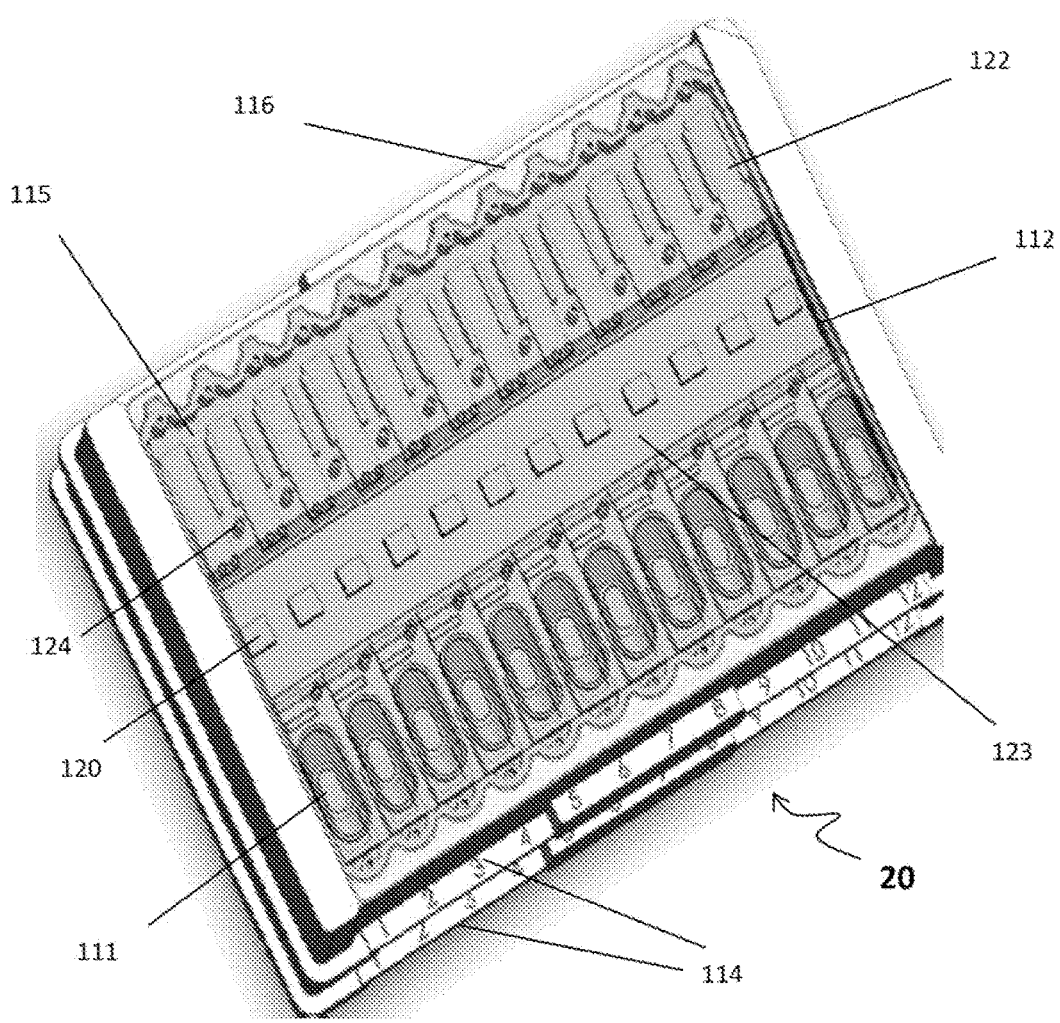
FIG. 32 shows a perspective view of two stacked immunochromatographic devices adapted for an existing plate reader or for a dedicated reader wherein the assay carrier is configured in the form of a multiwell tissue culture plate.

FIG. 32 depicts two stacked devices \20 providing the sample access ovals 111 and the apertures 112. In this embodiment, the lid 110, including the lid surface 116, is transparent.

Figure 33:
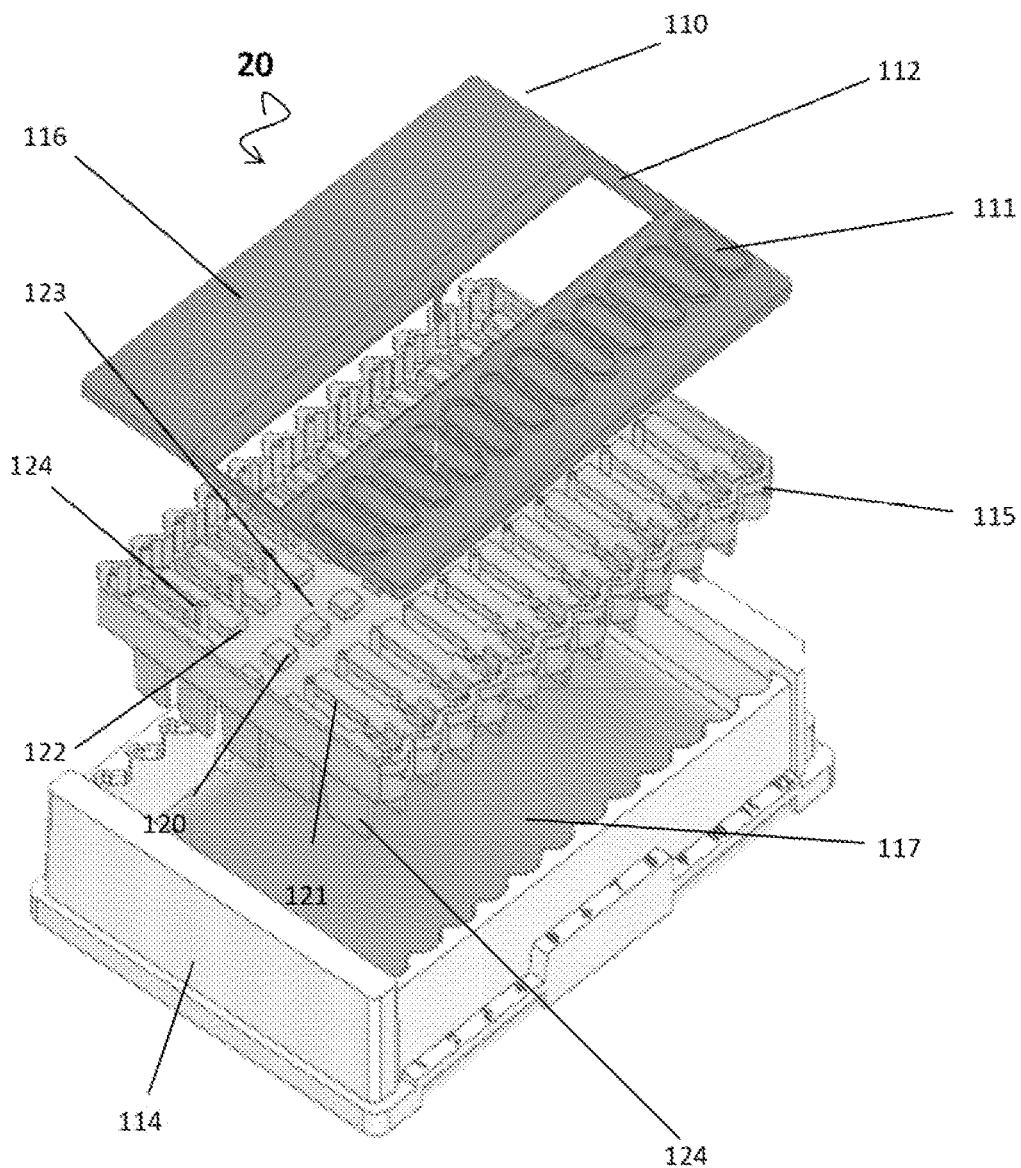
FIG. 33 shows another exploded view of an immunochromatographic device adapted for a plate reader, detailing the posts underneath the second component or portion.

FIG. 33 is another exploded view of the three portions 110,114,115 intended for use in an existing microtiter plate reader, which can be introduced into a reader using a movable tray, a draw mechanism, a belt-controlled mechanism and so on, which can be controlled by computer.

The invention relates in part to a device that enables consecutive or sequential running of plural assays in a single device, which in turn can be analyzed, that is, read, in an automated device which can determine the presence of and amount of complex at a test or capture site by measuring the amount of report at the site. Thus, a device can enable two or more assays to be configured therein. The number of assays that can be configured is a design choice and can be determined by the intended use of the device, and the intended automated reading device that will be used. Thus, a device of interest, can contain 3 CSPs, 4, 5, 6, 7, 8, 9, 10, 11, 12, 13, 14, 15, 16, 17, 18, 19, 20, 21, 22, 23, 24 CSPs or more. The device of interest can contain a corresponding number of channels to accept the CSPs. The CSPs can be of a length of design choice and a device can be configured to contain a plurality of CPSs arranged in parallel in a single row, or a device can be configured to contain two or more rows of CSPs. Thus, a device can contain one row of 8 CPSs to enable 8 tests, or two rows of 8 CSPs to enable 16 tests and so on as a design choice.

In another embodiment, the LFA device is adapted to engage an existing reading device format by disposing of an existing sample containing means, that is, a supporting structure, into an extant platform to accommodate one or more LFA assay means. In one aspect, a housing found on a unit device or ticket as taught herein is disregarded and the individual CSPs are retained in the LFA device (see, e.g., FIG. 28). Such an embodiment could increase the number of assays that can be housed in the LFA device, and the assays may be conducted simultaneously, and read simultaneously. The reader may be one which determines presence of reporter on each CSP individually, in small groups or all CSPs can be read simultaneously. Thus, the individual CSPs may be retained at sites or voids on a support structure. The LFA device of the present invention may contain adhesive means, a mechanical means, such as a superior lid or cover means which rests on the strips and support structure to affix the membranes in place, for example. Also, the individual strips may be affixed in a manner that provides each strip with a channel or void that is separate from that of the adjacent strip to provide a dedicated void for each strip or membrane. That may be accomplished, for example, with a barrier means, such as a wall or ridge running parallel to the strip of membrane, thin lines of hydrophobic material, such as, a hydrophobic polymer, a petrolatum, configured along the length of the support structure, essentially forming channels. The support structures are configured to enable a means for adding sample, a means for adding fluids, if needed, and a means to detect presence of reporter at the reaction site. The means for adding fluids may be voids in a covering or lid; a covering or lid that permits visualization;

and the like. In another embodiment, the lid is also transparent, for example, to an incident illumination, or other form of electromagnetic radiation, where the angle of illumination or incident electromagnetic radiation may be perpendicular to the support structure or at an acute angle to the support structure, that is, the source is superior or to the side of the LFA device. In yet another embodiment, the inferior side or bottom side of the lid is configured to contain one or more various ridges, pegs, protrusions, forms and the like in a format and size to provide corresponding guides, restraints, controls and other physical barriers and the like, as stabilizing structures in register with that present on the support of the CSP, pads and the like to assist in maintaining or to restrain the components, such as the CSP and pads in place, for example, to ensure good fluid communication, to provide further barriers to separate adjacent assay strips, to control capillary fluid flow along the CSP and so on.

Solely for the purpose of exemplification, several figures are presented where a device enables an LFA to be read in an existing plate reader or may be conducted and read in a plate reader. A device of interest can be adapted to be read in any other existing reading device.

In another embodiment, the invention relates to a dedicated and an integrated automated system for reading the multiple assay LFA device of the present invention with a reading device dedicated to the format of the multiple assay LFA device as described. Hence, a reading device may comprise a means to transport and to deliver (e.g., a receiving means), such as a computer-controlled robotic arm, a belt, a gearing system and so on, the LFA device into the reading device for access to a sensing means therein. After the multiple assays are scanned, read, analyzed and the like, the transport means or delivering means may move the LFA device from the sensing means to a storage area for holding means already tested.

The reading device may comprise a data processing means, such as, a CPU, a data storage means, such as, a tape, a disk, a hard disk drive, a RAM, a ROM, a microchip and so on, a data presentation means, such as an LCD, a CRT and the like, a data reproducing or printing means and the like to provide data analysis, data presentation and data storage. The reading device may contain a data communication means to provide transfer of data to other devices via a LAN, a WAN, a WLAN, a WWAN and so on.

The reading device may optionally include a liquid handling means, such as a suitably equipped robotic arm, to enable sample addition to the individual sample access sites of an LFA device. Hence, samples may be loaded on or in a sample holding means, such as a carousel or other dedicated sample holder and an aliquot is removed therefrom by the liquid handling device to provide a sample for testing in an LFA device of the present invention by application of the sample by the sample access. The sample delivery means may be instructed to a vessel comprising a buffer, a salt or other suitable liquid wash solution to enable a purging of any sample from the interior of the sample delivery means, such as a needle or a pipet, between samples.

To ensure identity of samples in such an automated system, individual samples may be tracked, for example, by a camera, or each sample may carry an identifying means, such as a bar code. Each LFA device will also include a unique test identifying means, such as a bar code, so that the reading device may track a sample by correlating the sample identifying means with the test identifying means. Thus, in the case of bar codes, the reading device will include a bar code-scanning or reading means. Hence, the reading results will be correlated to a particular immunoassay, and that immunoassay will be correlated with a particular sample, and hence, a patient.

In one embodiment, an assay of interest is used in the development and design of a drug. Drug candidates can be screened against a panel of samples from a random or target population to determine whether the drug candidate contains epitopes or cross reactive or immunogenic sites that are recognized in the subpopulation or test population, and if so, to what extent, as inferred by antibody thereto. That data will provide a baseline of an expected level of cross reactivity and/or side effects in the anticipated population from which the panel of samples was obtained. The drug candidate can be manipulated to avoid immunogenicity by altering drug structure and retesting as taught herein.

In another embodiment, an assay of interest is used to determine whether a patient will be a suitable candidate for inclusion in a drug treatment regimen. The patient is tested to determine whether existing cross reactive ADA is present.

An instant assay also is used to monitor the status of a patient while on a drug treatment regimen. The patient monitoring can be done periodically while the patient is receiving the drug. Presence of ADA indicates possible or anticipated reduced efficacy. Hence, either the dosage is increased or the patient is placed on an alternative drug.

Because plural drugs may carry the same or similar substituents, groups and the like, reactivity to one drug may signal possible or likely reactivity to another drug carrying the same or similar substituent, group and the like. Hence, a patient taking one drug can be tested for ADA, and if ADA is present, the patient is tested to determine whether that ADA reacts with a second or other drug, or patient antibody can be tested for reactivity with the second or other drug.

In other embodiments, an assay of interest can be used to ascertain whether a host has generated an antibody response to an antigen of interest, such as a food allergen, an environmental allergen or a self-antigen, in cases of pathology, such as an allergy. Hence, the instant assay can be used to ascertain whether a host has an allergy to a certain food, such as gluten, wheat and so on; an environmental antigen, such as pollen of certain plants, dander and so on; an autoimmune disease arising from autoantibody to myelin, nucleic acids, various organs, such as the thyroid, such as in Grave's disease, and so on leading to such diseases in human such as, celiac disease, rheumatoid arthritis, myasthenia gravis, diabetes and so on.

The instant invention now will be exemplified in the following non-limiting examples.

EXAMPLES

Example 1. Biotin and Hapten Conjugation Methods

The PEG and IgG molecules are used as a generic example for the conjugation of PEG or drug molecules with biotin and haptens such as DNP, digoxigenin, digoxin, fluorescein, thyroxine, THC, morphine, amphetamine, heroin, barbiturates or other tags. Other conjugations of peptide, protein, and DNA/RNA drugs were prepared in a similar manner.

Method 1. Conjugation of 40 kDa PEG with a Biotin (without a Linker).

PEG-$NH_2$ (MW 40,000, NOF Corporation) (1.33 mg) was dissolved in 1 mL of PBS (BupH phosphate buffered saline from Thermo). N-hydroxysuccinimidobiotin (EZ-Link NHS-Biotin from Thermo) (113 µg) was dissolved in 33.3 uL of dimethyl sulfoxide (DMSO). The solution was then added to the PEG solution. The reaction was incubated for 1 hour at room temperature. The product was purified on a desalting column, by ultrafiltration, or dialysis.

Method 2. Conjugation of 40 kDa PEG with a Digoxigenin (without a Linker).

PEG-NH$_2$ (MW 40,000, NOF Corporation) (1.33 mg) was dissolved in 1 mL of PBS (BupH phosphate buffered saline from Thermo). E-(Digoxigenin-3-O-acetamido)caproic acid N-hydroxysuccinimide ester (Sigma-Aldrich) (219.6 µg) was dissolved in 33.3 uL of DMSO which then was added to the PEG solution. The reaction was incubated for 1 hour at room temperature. The product was purified on a desalting column, by ultrafiltration, or dialysis.

Method 3. Conjugation of 40 kDa PEG with a DNP (without a Linker).

PEG-NH$_2$ (MW 40,000, NOF Corporation) (1.33 mg) was dissolved in 1 mL of PBS (BupH phosphate buffered saline from Thermo). 2,4-Dinitrophenyl-N-hydroxysuccinimide (Cisbio) (131.3 µg) was dissolved in 33.3 uL of dimethyl sulfoxide, which then was added to the PEG solution. The reaction was incubated for 1 hour at room temperature. The product was purified on a desalting column, by ultrafiltration, or dialysis.

Method 4. Conjugation of Mouse IgG with Biotin (without a Linker).

Two mg of mouse IgG were dissolved in 2 mL of PBS (BupH phosphate buffered saline from Thermo). Forty-five µg of N-hydroxysuccinimidobiotin (EZ-Link NHS-Biotin from Thermo) was dissolved in 13.2 uL of water and that was added to the mouse IgG solution. The reaction was incubated for 1 hour at room temperature. The product was purified on a desalting column, by ultrafiltration, or dialysis.

Method 5. Conjugation of Mouse IgG with Biotin (with a Linker).

Two mg of mouse IgG were dissolved in 2 mL of PBS (BupH phosphate buffered saline from Thermo). EZ-Link NHS-PEG$_4$-Biotin (Thermo) (77.7 µg) was dissolved in 13.2 uL of water and then added to the mouse IgG solution. The reaction was incubated for 1 hour at room temperature. The product was purified on a desalting column, by ultrafiltration, or dialysis.

Method 6. Conjugation of Mouse IgG with Digoxigenin (without a Linker).

Two mg of mouse IgG were dissolved in 2 mL of PBS (BupH phosphate buffered saline from Thermo). ε-(Digoxigenin-3-O-acetamido)caproic acid N-hydroxysuccinimide ester (Sigma-Aldrich) (86.96 µg) was dissolved in 13.2 uL of DMSO and that was added to the mouse IgG solution. The reaction was incubated for 1 hour at room temperature. The product was purified on a desalting column, by ultrafiltration, or dialysis.

Method 7. Conjugation of Mouse IgG with Digoxigenin (with a Linker).

Four mg of mouse IgG were dissolved in 1 mL of 0.1M sodium phosphate (5 mM EDTA, pH 6.0). Six mg of 2-mercaptoethylamine.HCl were added to the mouse IgG solution. The reaction was incubated at 37° C. for 90 minutes. The reduced IgG was purified on a desalting column, by ultrafiltration or dialysis, and concentrated to a volume of 1 mL of PBS (BupH phosphate buffered saline from Thermo). N-(κ-maleimidoundecanoic acid) hydrazide, trifluoroacetic acid salt (Thermo) (109 µg) was dissolved in 26.6 uL of dimethyl sulfoxide which then was added to the mouse IgG solution. The reaction was incubated for 2 hours at room temperature. The reaction mixture was purified on a desalting column, by ultrafiltration, or dialysis with 2-(morpholino)ethanesulfonic acid (0.9% NaCl, Thermo, pH 4.7). ε-(Digoxigenin-3-O-acetamido)caproic acid N-hydroxysuccinimide ester (Sigma-Aldrich) (175 µg) was dissolved in 26.6 uL of DMSO which then was added to the activated mouse IgG solution. The reaction was incubated at room temperature for 1 hour. The product was purified on a desalting column, by ultrafiltration, or dialysis.

Method 8. Conjugation of Mouse IgG with DNP (without a Linker).

Two mg of mouse IgG were dissolved in 2 mL of PBS (BupH Phosphate Buffered Saline from Thermo). Fifty-two µg of 2,4-dinitrophenyl-N-hydroxysuccinimide (Cisbio) were dissolved in 13.2 uL of dimethyl sulfoxide followed by being added into the mouse IgG solution. The reaction was incubated for 1 hour at room temperature. The product was purified with a desalting column, ultrafiltration, or dialysis.

Method 9. Conjugation of Mouse IgG with DNP (with a Linker).

Four mg of mouse IgG were dissolved in 1 mL of 0.1M sodium phosphate (5 mM EDTA, pH 6.0). Six mg of 2-mercaptoethylamine.HCl were added to the mouse IgG solution. The reaction was incubated at 37° C. for 90 minutes. The reduced IgG was purified on a desalting column, by dialysis or ultrafiltration and concentrated to a volume of 1 mL of PBS (BupH phosphate buffered saline from Thermo). N-(κ-maleimidoundecanoic acid) hydrazide, trifluoroacetic acid salt (Thermo) (109 µg) was dissolved in 26.6 uL of dimethyl sulfoxide which was added to the mouse IgG solution. The reaction was incubated for 2 hour at room temperature. The reaction mixture was purified using a desalting column, by dialysis or ultrafiltration with 2-(morpholino)ethanesulfonic acid (0.9% NaCl, Thermo, pH 4.7). 2,4-dinitrophenyl-N-hydroxysuccinimide (Cisbio) (104.8 µg) was dissolved in 26.6 uL of dimethyl sulfoxide which then was added to the mouse IgG solution. The reaction was incubated at room temperature for 1 hour. The product was purified on a desalting column, by ultrafiltration, or dialysis.

Method 10. Conjugation of Mouse IgG with a Biotin (without a Linker) Using an Aldehyde Functional Group.

Two mg of mouse IgG were dissolved in 1 mL of 0.1 M sodium acetate buffer (pH 5.5, Thermo). Sodium metaperiodate (Thermo) (2.1 mg) was added to the mouse IgG solution. The reaction was incubated for 30 minutes at room temperature in the dark then purified on a desalting column, by dialysis or ultrafiltration and concentrated to 900 uL of PBS. Biotin hydrazide (EZ-Link Biotin Hydrazide from Thermo) (1.29 mg) was dissolved in 100 uL of DMSO which then was added to the activated mouse IgG solution and incubated at room temperature for 2 hours. The product was purified on a desalting column, by ultrafiltration, or dialysis.

Method 11. Conjugation of Mouse IgG with a Biotin (with a Linker) Using an Aldehyde Functional Group.

Two mg of mouse IgG was dissolved in 1 mL of 0.1 M sodium acetate buffer (pH 5.5, Thermo). Sodium metaperiodate (Thermo) (2.1 mg) was added to the mouse IgG solution. The reaction was incubated for 30 minutes at room temperature in dark then purified on a desalting column, by dialysis or ultrafiltration and concentrated into 900 uL of PBS. Biotin-dPEG™$_4$-hydrazide (Quanta Biodesign) (2.53 mg) was dissolved in 100 uL of DMSO which then was added to the activated mouse IgG solution and incubated at room temperature for 2 hours. The product was purified on a desalting column, by ultrafiltration, or dialysis.

Method 12. Conjugation of Mouse IgG with a Biotin (without a Linker) Using Carboxyl Functional Group.

Five mg of mouse IgG were dissolved in 962.5 µL of 2-(morpholino) ethanesulfonic acid (0.9% NaCl, Thermo, pH 4.7). Biotin hydrazide (EZ-Link Biotin Hydrazide from Thermo) (323 µg) was dissolved in 25 µL of DMSO which then was added to the mouse IgG solution. 1-Ethyl-3-(3-dimethylaminopropyl) carbodiimide hydrochloride (1.25 mg) was dissolved in 12.5 µL of 2-(morpholino) ethanesulfonic acid (0.9% NaCl, Thermo, pH 4.7), which then was added to the mouse IgG solution. The reaction was incubated at room temperature for 2 hours. The product was purified on a desalting column, by ultrafiltration, or dialysis.

Method 13. Conjugation of Mouse IgG with a Biotin (with a Linker) Using Carboxyl Functional Group.

Five mg of mouse IgG were dissolved in 962.5 µL of -(morpholino)ethanesulfonic acid (0.9% NaCl, Thermo, pH 4.7). Biotin-dPEG™$_4$-hydrazide (Quanta Biodesign) (632 µg) was dissolved in 25 µL of DMSO, which then was added to the mouse IgG solution. 1-Ethyl-3-(3-dimethylaminopropyl) carbodiimide hydrochloride (1.25 mg) was dissolved in 12.5 uL of (morpholino)ethanesulfonic acid (0.9% NaCl, Thermo, pH 4.7) and that solution was added to the mouse IgG solution. The reaction was incubated at room temperature for 2 hours. The product was purified on a desalting column, by ultrafiltration, or dialysis.

Method 14. Conjugation of Mouse IgG with a Biotin (without a Linker) Using a Maleimide Functional Group.

Two mg of mouse IgG were dissolved in 1 mL of 0.1M sodium phosphate (5 mM EDTA, pH 6.0). Six mg of 2-mercaptoethylamine.HCl were added to the mouse IgG solution. The reaction was incubated at 37° C. for 90 minutes. The reduced IgG was purified on a desalting column then equilibrated with PBS (BupH phosphate buffered saline from Thermo). 1-Biotinamido-4-[4'-(maleimidomethyl) cyclohexanecarboxamido] butane (71 µg) was dissolved in 13 µL of DMSO which then was added to the mouse IgG solution. The reaction was incubated at room temperature for 2 hours. The product was purified on a desalting column, by ultrafiltration, or dialysis.

Method 15. Conjugation of Mouse IgG with a Biotin (with a Linker) Using a Maleimide Functional Group.

Two mg of mouse IgG were dissolved in 1 mL of 0.1M sodium phosphate (5 mM EDTA, pH 6.0). Six mg of 2-mercaptoethylamine.HCl were added to the mouse IgG solution. The reaction was incubated at 37° C. for 90 minutes. The reduced IgG was purified on a desalting column then equilibrated with PBS (BupH phosphate buffered saline from Thermo). EZ-Link® Maleimide-PEG$_{11}$-Biotin (Thermo) (243 µg) was dissolved in 26 µL of DMSO, which then was added to the mouse IgG solution. The reaction was incubated at room temperature for 2 hours. The product was purified on a desalting column, by ultrafiltration or dialysis.

Method 16. Conjugation of Mouse IgG with a Biotin (without a Linker) Using Iodoacetamide Group.

Four mg of mouse IgG were dissolved in 1 mL of 0.1M sodium phosphate (5 mM EDTA, pH 6.0). Six mg of 2-mercaptoethylamine.HCl were added to the mouse IgG solution. The reaction was incubated at 37° C. for 90 minutes. The reduced IgG was purified on a desalting column then equilibrated with 50 mM Tris-HCl (5 mM EDTA, pH 8.0-8.3) and concentrated to a volume of 1 mL. One hundred µg of N-iodoacetyl-N-biotinylhexylenediamine (Thermo) were dissolved in 50 µl, of dimethylformamide (DMF) followed by adding that solution to the reduced mouse IgG solution. The reaction was incubated at room temperature in the dark for 90 minutes. The product was purified on a desalting column, by ultrafiltration, or dialysis.

Method 17. Conjugation of Mouse IgG with a Biotin (with a Linker) Using Iodoacetamide Group.

Four mg of mouse IgG were dissolved in 1 mL of 0.1M sodium phosphate (5 mM EDTA, pH 6.0). Six mg of 2-mercaptoethylamine.HCl were added to the mouse IgG solution. The reaction was incubated at 37° C. for 90 minutes. The reduced IgG was purified on a desalting column, by ultrafiltration or dialysis, equilibrated with 50 mM Tris-HCl (5 mM EDTA, pH 8.0-8.3) and concentrated to a volume of 1 mL. One hundred and ten µg of biotinyl-iodoacetamidyl-3,6-dioxaoctanediamine (Thermo) was dissolved in 50 of 50 mM Tris.HCl (5 mM EDTA, pH 8.0-8.3) and that solution was added to the reduced mouse IgG solution. The reaction was incubated at room temperature in the dark for 90 minutes. The product was purified on a desalting column, by ultrafiltration or dialysis.

Method 18. Conjugation 40 kDa PEG with a Biotin (without a Linker).

Aminoxy PEG (MW 40,000, NOF) was conjugated with a biotin in a similar manner to Method 1.

Method 19. Conjugation of 40 kDa PEG with a Digoxigenin (without a Linker).

Aminoxy PEG (MW 40,000, NOF) was conjugated with a digoxigenin in a similar manner to Method 2.

Method 20. Conjugation of 40 kDa PEG with a DNP (without a Linker).

Aminoxy PEG (MW 40,000, NOF) was conjugated with a DNP in a similar manner to Method 3.

Other PEG-biotin and PEG-hapten conjugates with PEG molecular weights ranging from 10 kDa to 50 kDa were prepared in a similar manner to that using 40 kDa PEG. Other peptide/protein-biotin and peptide/protein-hapten conjugates were prepared in a similar manner to that using IgG. Conjugates with linkers or spacers such as PEGs with molecular weights ranging from 88 to 20,000; linkers containing hydrocarbons ranging from one carbon atom to twenty two carbon atoms, aromatic rings, hetero atoms other than carbon (e.g., N, O, S, P, etc.), and/or a combination thereof; proteins (i.e., albumins or IgGs from bovine, human, rabbit, mouse, rat, goat and/or other sources), branched polymers (e.g., branched PEG polymers and other symmetrically and asymmetrically branched polymers with homo- and hetero-bi- and multi-functional groups) were all prepared in a similar manner.

Example 2. Preparation of Branched Polymer Conjugates

Preparation of Protein-Randomly Branched Polymer Conjugates

The preparation of a randomly branched (RB) mixed (m) surface (OH/NH$_2$ mix) m-RB-PEI-NH$_2$/OH-2-protein (PEI is polyethyleneimine) conjugate is provided as a general procedure for the preparation of branched polymer-polypeptide conjugates. Other conjugates such as PEI-protein, m-RB-PEI-NH$_2$-1-protein, m-RB-PEI-NH$_2$-2-protein, m-RB-PEI-NH$_2$-3-protein, m-RB-PEI-NH$_2$-4-protein, as well as m-RB-PEI-NH$_2$/OH-1 (OH/NH$_2$ mix)-protein, m-RB-PEI-NH$_2$/OH-2 (OH/NH$_2$ mix)-protein, and m-RB-PEI-NH$_2$/OH-3 (OH/NH$_2$ mix)-protein conjugates were synthesized in a similar manner.

LC-SPDP-Mixed Surface m-RB-PEI-NH$_2$/OH-2:

To a mixed surface randomly branched m-RB-PEI-NH$_2$/OH-2 (400×10$^{-9}$ mol) in 400 ml of phosphate buffer (20 mM phosphate and 0.1 M NaCl, pH 7.5) were added 4.0×10$^{-6}$ mol of sulfo-LC-SPDP (succinimidyl 6-(3-[2-pyridyldithio]-propionamido)hexanoate containing a long chain (LC)

spacer, Pierce/Thermo Scientific) in 400 ml of water. The mixture was vortexed for and incubated at 30° C. for 30 minutes. The LC-SPDP-m-RB-PEI-NH$_2$/OH-2 was purified by gel filtration chromatography and equilibrated with buffer A (0.1 M phosphate, 0.1 M NaCl and 5 mM EDTA, pH 6.8). The product was further concentrated to yield 465 ml of solution, with a concentration of approximately 0.77 nmol/µmol.

Thiolated m-RB-PEI-NH$_2$/OH-2 from LC-SPDP m-RB-PEI-NH$_2$/OH-2:

LC-SPDP m-RB-PEI-NH$_2$/OH-3 (50 nmol in 65 ml of buffer A) was mixed with 100 ml of dithiothreitol (DTT) (50 mM in buffer A) and was allowed to incubate at room temperature for 15 minutes. Excess DTT and byproducts were removed by gel filtration with buffer A. The product was concentrated in a 10 K Centricon Concentrator to yield 390 ml of the thiolated m-RB-PEI-NH$_2$/OH-2 that was used for conjugation with activated antibody.

Maleimide R (MAL-R) Activated Protein:

To the protein in PBS (310 µL, 34 nmol) was added 20.4 ml of a MAL-R-NHS (N-hydroxysuccinimide) solution (10 mM in water). The mixture was vortexed and incubated at 30° C. for 15 minutes. The product was purified by gel filtration with buffer A. The maleimide-R activated protein was used for conjugation with the thiolated m-ran-AB-PEI-NH$_2$/OH-2.

m-RB-PEI-NH$_2$/OH-2-Protein Conjugate:

To the thiolated m-RB-PEI-NH$_2$/OH-2 (310 ml or 35.7 nmol) was added the MAL-R activated protein (4.8 mL or 34 nmol). The reaction mixture was concentrated to approximately 800 ml, which then was allowed to incubate overnight at 4° C., and at room temperature for about 1 hr. On completion, the reaction was quenched with 100 µL of ethyl maleimide (50 mmolar solution), and the conjugate was then fractionated on a carboxymethyl cellulose column (5 ml) with a sodium chloride step gradient in 20 mM phosphate buffer at pH 6. The conjugate was eluted with a sodium chloride gradient, and characterized by cationic exchange chromatography, UV spectroscopy, and polyacrylamide gel electrophoresis.

Conjugation Via Reductive Coupling

Reduction of Protein:

To the protein, 14 nmol in 160 µL of buffer B (containing 0.1 M sodium phosphate, 5 mM EDTA, and 0.1 M NaCl, pH 6.0) were added 40 µL of DTT (50 mM in buffer B). The solution was allowed to stand at room temperature for 30 min. The product was purified by gel filtration in a Sephadex G-25 column equilibrated with buffer B. The reduced protein was concentrated to 220 µL, and was used for the following conjugation.

MAL-R-Mixed Surface RBP:

To the mixed surface RBP in 400 µL (400×10$^{-9}$ mols) at pH 7.4 were added 400 µL of MAL-R-NHS (10 mM in water). That was mixed and incubated at 30° C. for 15 min. On termination, the product was purified on a Sephadex G-25 column equilibrated with buffer B. The MAL-R-mixed surface RBP was collected and stored in aliquots in the same buffer at −40° C.

Mixed Surface RBP-Protein Conjugate:

To the reduced protein (14 nmols in 220 µL) was added the MAL-R-mixed surface m-RB-PEI-NH$_2$/OH-2 (154 µL, 16.6 nmols) with stirring. To that mixture were added 12.5 µL of sodium carbonate (1.0 M solution) to bring the pH to ~6.8. The reaction was continued for 1 hr at room temperature. The reaction was terminated with the addition of 100 µL of cysteamine (0.4 mM solution). The conjugation mixture was purified on a CM cellulose column with a sodium chloride gradient elution.

The preparation of other protein-asymmetrically/symmetrically branched polymer conjugates, including streptavidin-asymmetrically/symmetrically branched polymer conjugates, were prepared in a similar manner.

Example 3. Preparation of Gold-Ab Conjugates

To a 125 ml flask were added 60 ml of colloidal gold solution (20-80 nm in diameter, O.D. 1.078). The pH of the solution was adjusted to 8-11 by addition of a 0.2 M potassium carbonate solution. To that solution were added 600 ml of conjugated antibody/streptavidin solution (O.D. 0.1-1.5 in sodium borate buffer) while stirring, followed by subsequent addition of 600 ml of bovine serum albumin (20% with sodium azide stabilizer). The mixture was stirred at 20° C. for 20-60 more minutes. The solution remained purple in color and some foaminess was observed. On completion, the stir bar was removed and the reaction mixture was transferred to two 50 ml conical tubes. The material was centrifuged until very little color was observed in the supernatant. The supernatant was removed and 400 ml of 25 mM sodium borate buffer were added to each tube. The contents were mixed thoroughly and the two tubes of material were combined and characterized by UV-Vis.

Example 4. Immunogenicity Assay for the Detection of Anti-Mouse IgG

Figure 3:
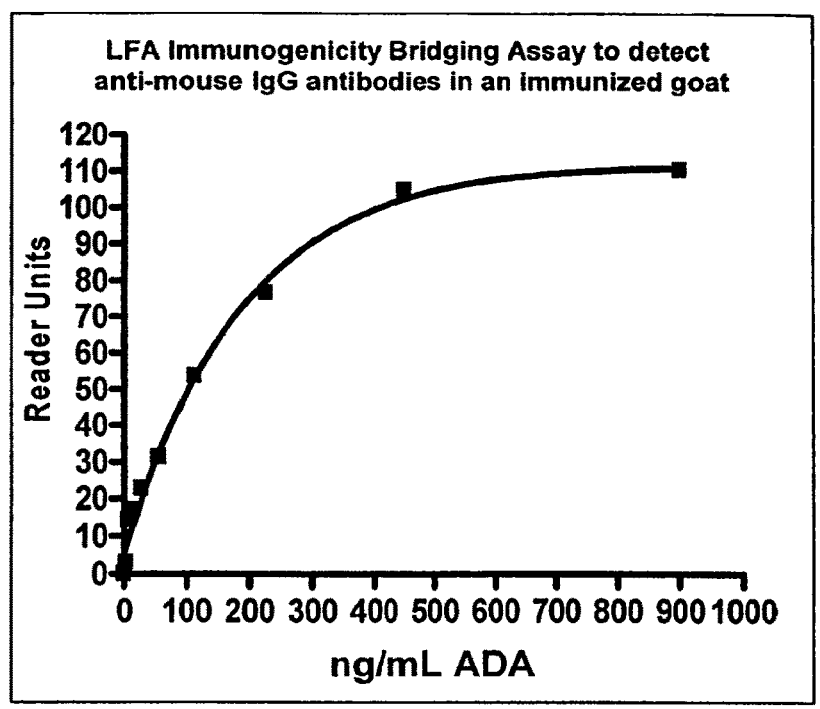
FIG. 3 provides a summary of data in the form of a graph showing a positive correlation between signal, as represented by reader units, on the ordinate, and level of antibody on the axis. The antigen detected, the ADA, was a goat anti-mouse IgG antibody. The capture reagent was a mouse IgG immobilized on a nitrocellulose membrane. The detector was a biotinylated mouse IgG. The reporter was streptavidin-coated gold.

A typical result obtained from a lateral flow assay design is shown in FIG. 3 wherein the drug is a mouse IgG, and the host is a goat that was exposed to the mouse IgG. The LFA format depicted in FIG. 2 was used to generate the dose response curve of FIG. 3 with serial dilutions of the goat antibodies, using an LFA test strip reader (LUR reader, ANP Technologies]. The limit of detection for that assay is 25 ng/mL ADA. The assay design can be used to detect ADA's to any type of therapeutic antibody.

Example 5. Detection of Anti-PEG/PEO Antibodies

An anti-PEG/PEO antibody detection assay is prepared in a similar manner as described herein except the drug or antibody is replaced by a PEG or PEO polymer. Various functionalized PEG/PEO polymers were purchased from commercial vendors.

Figure 4:
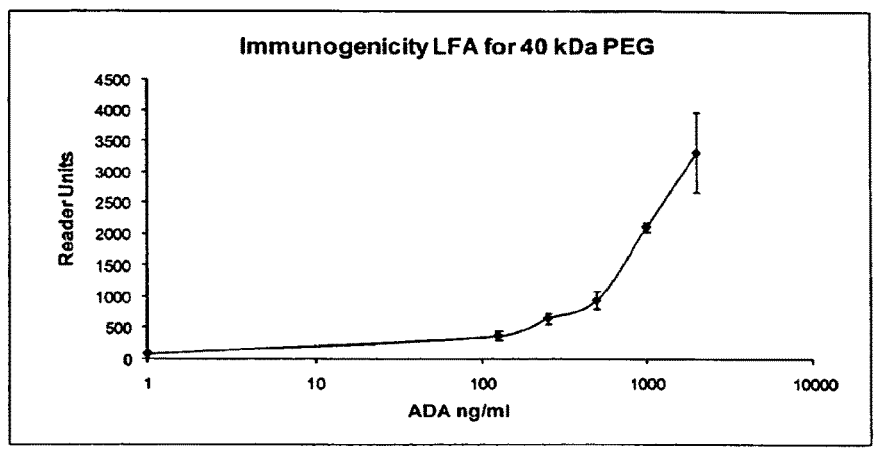
FIG. 4 summarizes data from an LFA for detecting antibodies that bind PEG. Hence, on the axis, the ADA is an antibody to PEG.

An immunogenicity assay was developed for 40 kDa PEG using an LFA format similar to that described in FIG. 1. The assay involved incubating the serum sample suspected of containing ADA with biotin-labeled PEG prepared according to Method 1 above, and digoxigenin-conjugated PEG prepared by Method 2 above for 20 minutes. Then 100 µL of the reaction mixture were applied to a lateral flow test strip containing releasable streptavidin-coated gold particles and a test zone that contained immobilized mouse anti-digoxigenin antibodies (Meridian Life Science). A dose response curve is shown in FIG. 4. A limit of detection of 125 ng/mL ADA was achieved. A mouse IgM anti-PEG (from Academia Sinica) was used as the positive control ADA in the assay.

Figure 5:
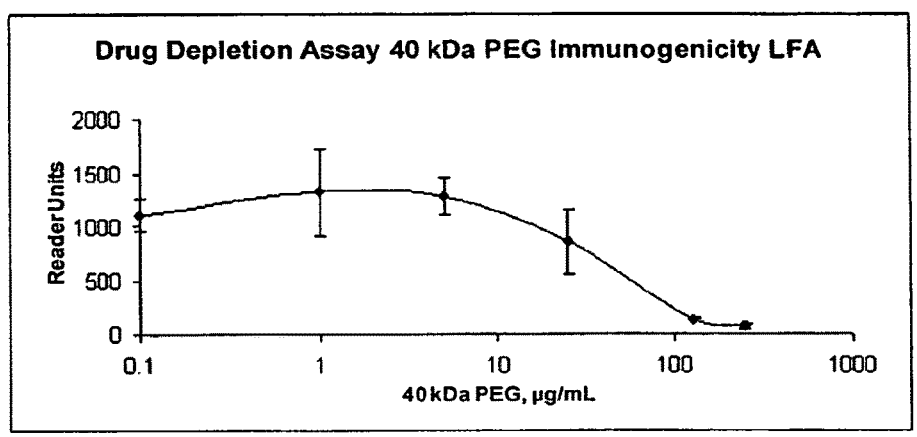
FIG. 5 summarizes data of a drug depletion assay where the specificity of the reaction is assessed by increasing levels of spiked antigen (e.g., PEG) resulting in decreasing signal. The ADA monitored was antibody to PEG. Essentially a competition assay, increasing levels of PEG in the reaction mixture prevented any anti-PEG antibodies (ADA) from reacting in the LFA, thereby reducing the formation of the bridge complexes, hence, reducing signal.

The specificity of the PEG immunogenicity LFA was validated with a drug depletion assay which shows that the ADA positive signal diminished with increasing amounts of 40 kDa PEG added to 500 ng/mL, of ADA solution and tested in the immunogenicity LFA (FIG. 5).

A handheld reader (SARII reader, ANP Technologies) was used to measure reporter on the tickets. The reader was calibrated using control samples and was designed to use a fixed cut off of 250 reader units to distinguish background from specific signal. Samples were spiked with graded amounts of free PEG to determine the level of the cut off. In the pattern recognition software employed by the reader, any detected signal below that value was considered noise or background. The fixed cut off point provides an advantage over the floating cut off points often used in ELISA formats.

Figure 6:
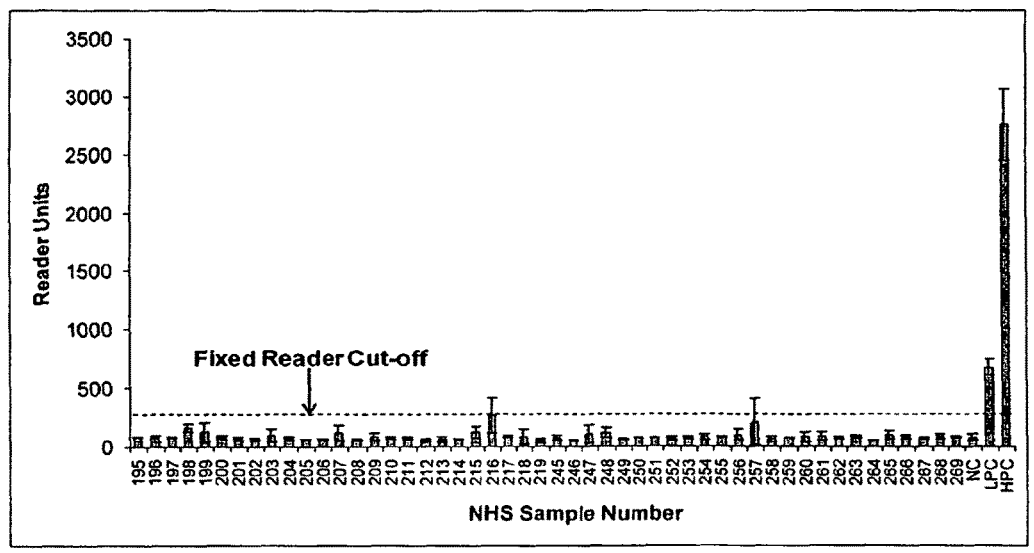
FIG. 6 summarizes the results of screening 50 normal human serum samples in a 40 kDa PEG immunogenicity LFA. Samples 216 and 257 were found to be weak or borderline positive and were retested and subjected to the drug depletion assay for confirmation. NC is a negative control, LPC is low positive control (125 ng/mL antibody) and HPC is high positive control (500 ng/mL).
Figure 7:
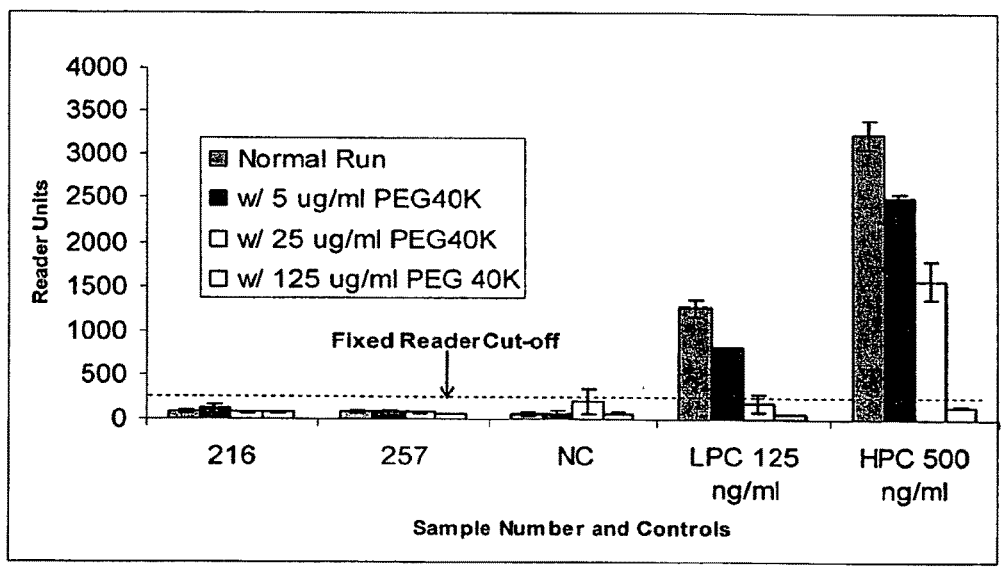
FIG. 7 shows the results of retesting borderline positive human samples in a drug depletion assay for the 40 kDa PEG immunogenicity LFA showing samples 216 and 257 to be true negatives.

Fifty normal human serum samples were tested with the 40 kDa PEG immunogenicity LFA. The results are presented in FIG. 6. Samples 216 and 257 were found to be weak or borderline positive and were retested and subjected to the drug depletion assay for confirmation. The results of the confirmation test show that both samples are true negatives (FIG. 7).

Example 6. Detection of Anti-Glucagon Antibodies

As an example of the ability of an assay of interest to detect antibodies to smaller proteins and peptides, an immunogenicity assay for glucagon (MW=3,485) (Bachem, Torrance, Calif.) was developed using the LFA format depicted in FIG. 1. In that embodiment, the anti-glucagon antibody detection assay is prepared in a similar manner as described above, except that the drug is glucagon.

Figure 8:
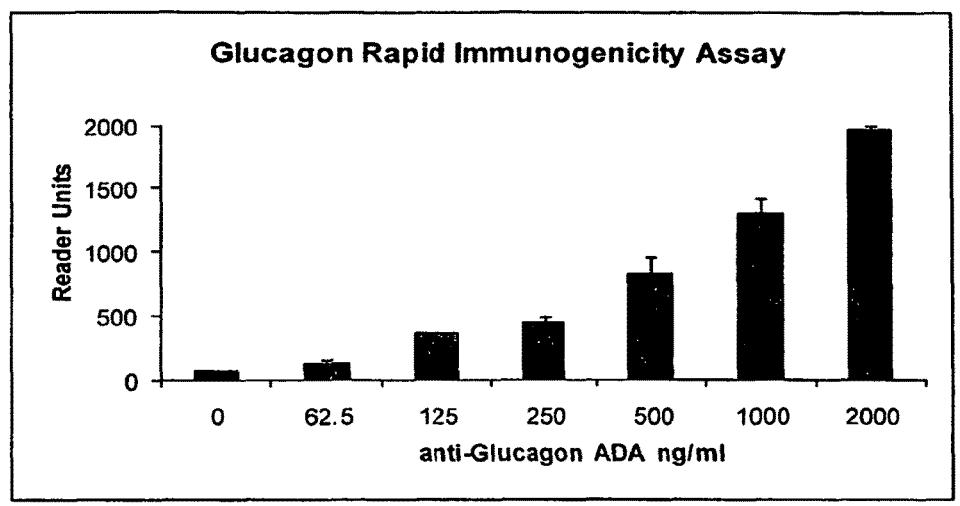
FIG. 8 depicts a dose response curve for an immunogenicity LFA for the detection of anti-glucagon ADAs.

The assay involved incubating the serum sample containing ADA with biotin-labeled glucagon (Bachem) and digoxigenin-conjugated glucagon, made as taught hereinabove, for 20 minutes then adding 100 uL of the reaction mixture to a lateral flow test strip containing releasable streptavidin-coated gold particles (see, for example, WO2005051295) and a test zone comprised of immobilized commercially available anti-digoxigenin antibodies. A dose response curve is shown in FIG. 8. A limit of detection of 125 ng/mL ADA was achieved. A rabbit anti-glucagon antibody (Bachem) was used as the ADA positive control in the assay.

Figure 9:
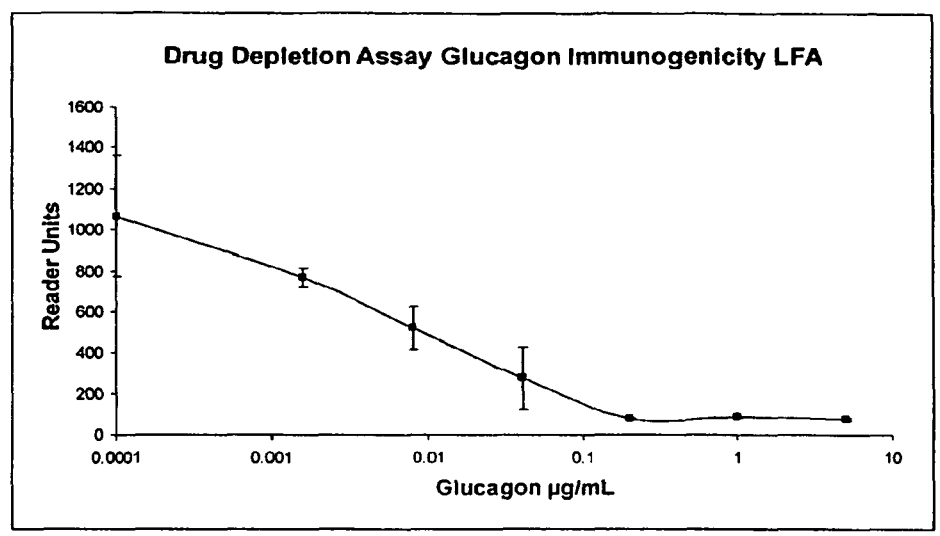
FIG. 9 summarizes data obtained from a drug depletion/competition assay curve for glucagon showing a decrease in signal with increasing amounts of spiked glucagon.

The specificity of the immunogenicity LFA was validated with a drug depletion assay where increasing concentrations of glucagon were added to an anti-glucagon positive control antibody (Bachem) and the samples tested in an LFA. That exercise showed that the ADA positive signal diminished with increasing amounts of glucagon added to 500 ng/mL of ADA and tested in the immunogenicity LFA (FIG. 9).

Figure 10:
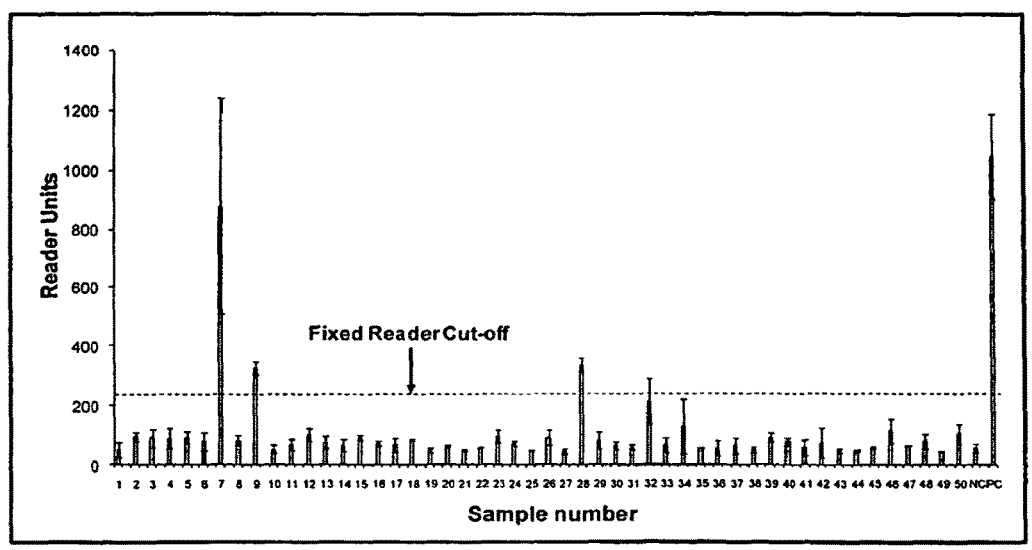
FIG. 10 shows the results of screening 50 normal human serum samples with the glucagon immunogenicity LFA. Samples 7, 9, 28, and 32 were found positive and were retested and subjected to the drug depletion assay for confirmation.
Figure 11:
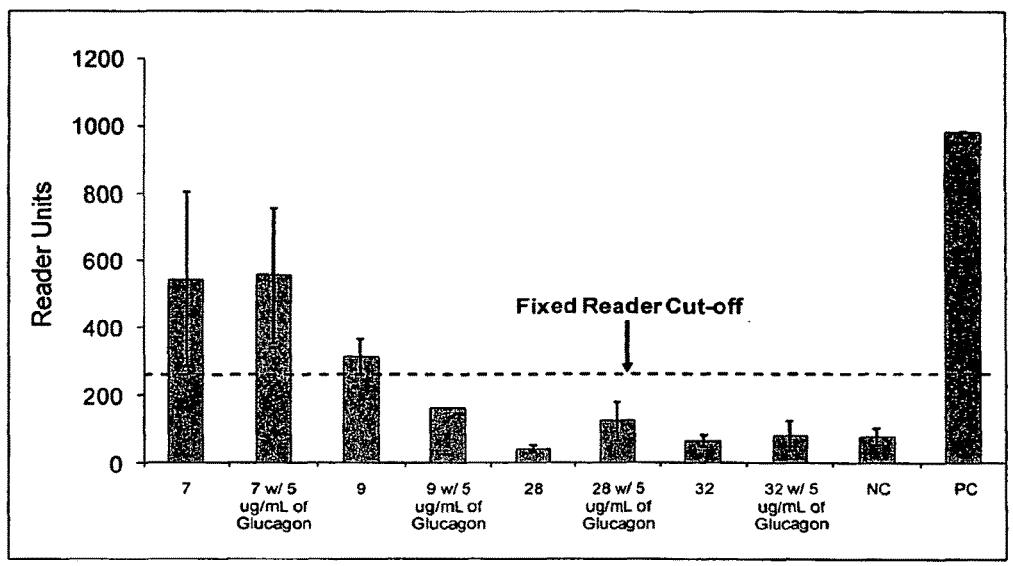
FIG. 11 summarizes the results of retesting apparent positive normal human samples in a glucagon depletion assay showing sample 7 to be a false positive, sample 9 to be a true weak positive, and samples 28 and 32 to be true negatives.

Fifty normal human serum samples were tested with the Glucagon immunogenicity LFA. The results are presented in FIG. 10. Samples 7, 9, 28, and 32 were found to be positive and were retested and subjected to the drug depletion assay for confirmation. The results of the confirmation test show that sample 7 is a false positive, sample 9 is a true positive and samples 28 and 32 are true negatives (FIG. 11).

Example 7. Detection of Anti-GLP-1 Antibodies

In another embodiment of the invention, the detection of antibodies to glucagon-like peptide-1 (GLP-1, MW=4,112) was obtained. The anti-GLP-1 antibody detection assay was prepared in a similar manner as described above, except that the drug is GLP-1.

Figure 12:
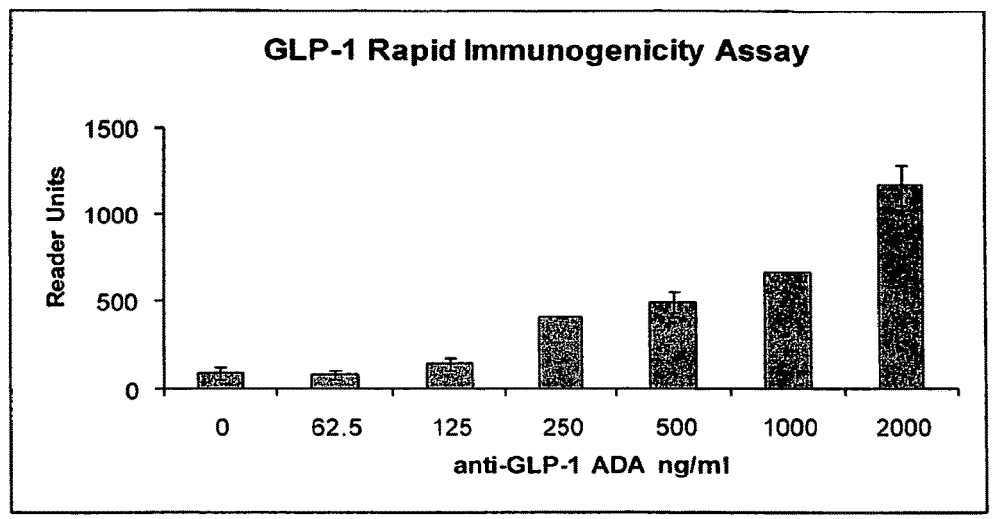
FIG. 12 depicts a dose response curve for an immunogenicity LFA for the detection of antibodies to GLP-1.

The assay involved incubating the serum sample containing ADA with biotin-labeled GLP-1 (Bachem) and digoxigenin-conjugated GLP-1 made as taught hereinabove for 20 minutes. Then 100 μL of the reaction mixture was added to a lateral flow test strip containing releasable streptavidin-coated gold particles and a test zone comprised of immobilized commercially available anti-digoxigenin antibodies. A dose response curve is shown in FIG. 12. A limit of detection of 250 ng/mL ADA was achieved. As a positive control, a rabbit anti-GLP-1 (Bachem) was used.

Figure 13:
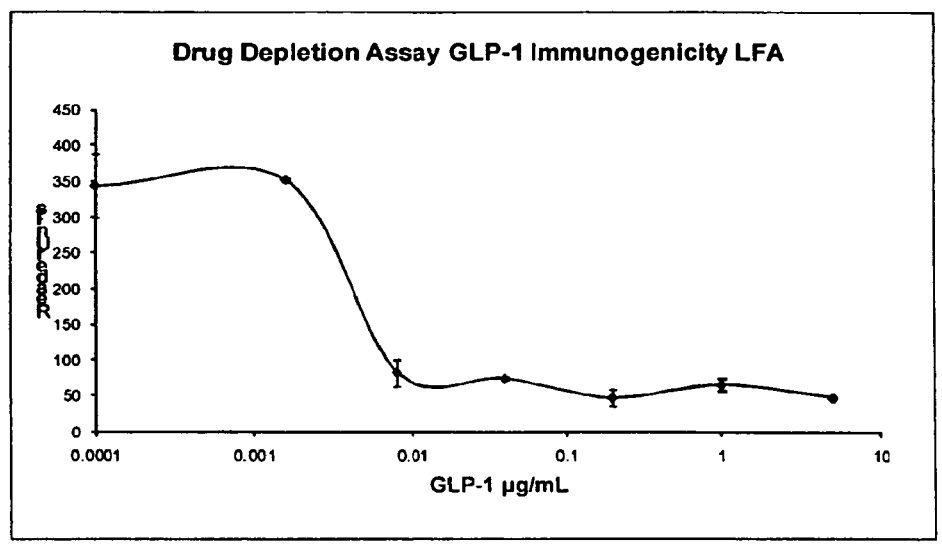
FIG. 13 summarizes data obtained from a drug depletion/competition assay for ADA to GLP-1 showing a decrease in signal with increasing amounts of spiked GLP-1.

The specificity of the immunogenicity LFA was validated with a drug depletion assay that shows that the ADA positive signal diminished with increasing amounts of GLP-1 added to 500 ng/mL of ADA and tested in the immunogenicity LFA (FIG. 13).

Figure 14:
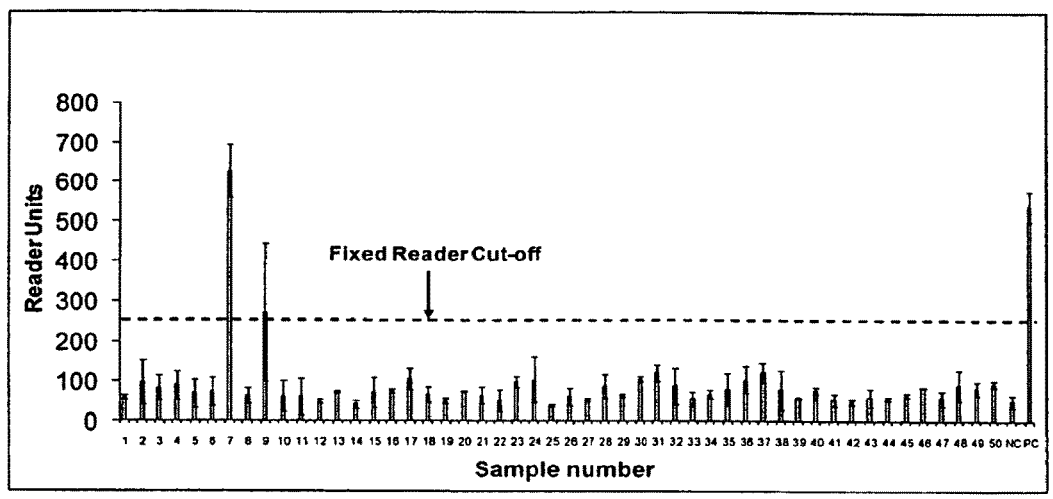
FIG. 14 shows the results of screening 50 normal human serum samples with the GLP-1 immunogenicity LFA. Samples 7 and 9 were found positive and were retested and subjected to the drug depletion assay for confirmation.
Figure 15:
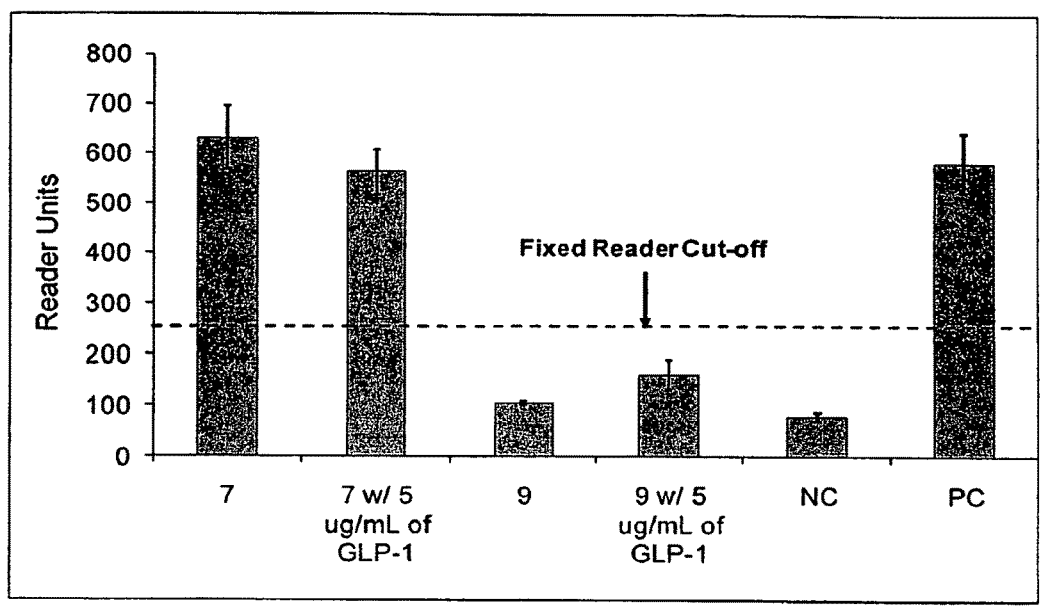
FIG. 15 presents the results of retesting of apparent positive normal human samples in a drug depletion assay showing sample 7 to be a false positive and sample 9 to be a true negative.

Fifty normal human serum samples were tested with the glucagon immunogenicity LFA. The results are presented in FIG. 14. Samples 7 and 9 were found to be positive and were retested and subjected to the drug depletion assay for confirmation. The results of the confirmation test show that sample 7 is a false positive, and sample 9 is a true negative (FIG. 15).

Figure 16:
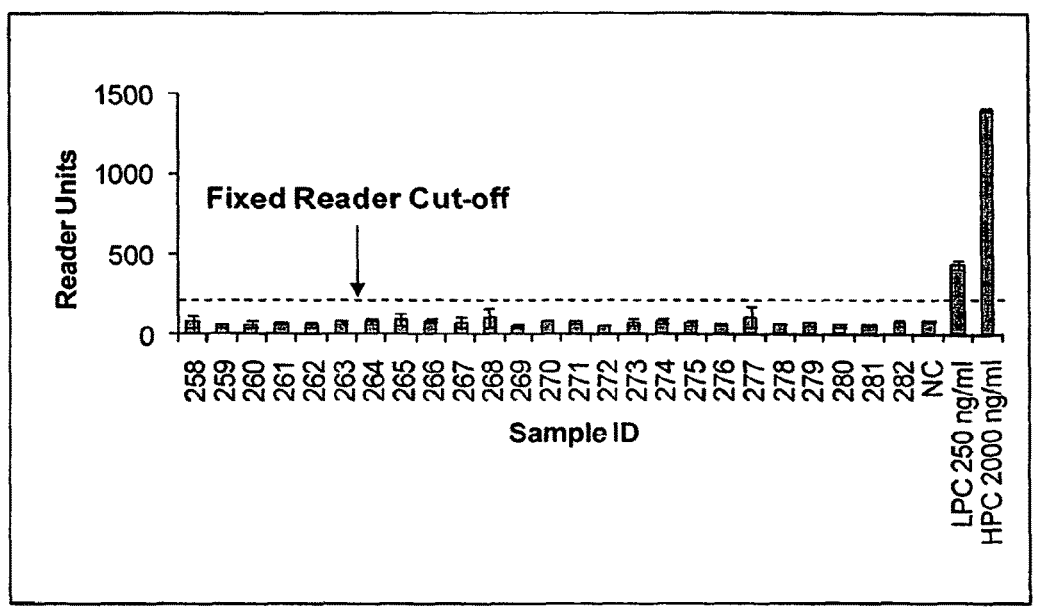
FIG. 16 shows the results of screening 25 obese human serum samples with the GLP-1 immunogenicity LFA. No sample was found positive.
Figure 17:
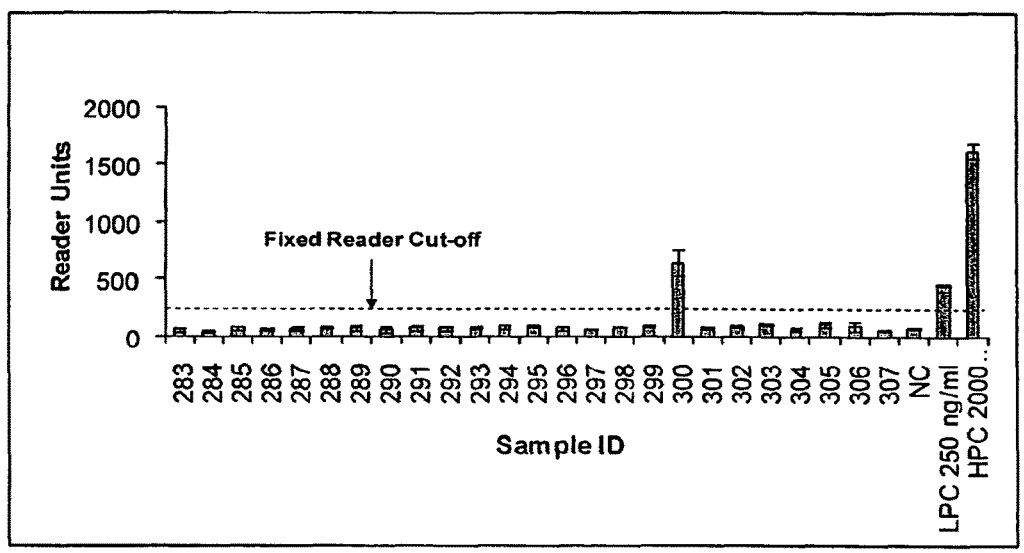
FIG. 17 summarizes the results of screening another 25 obese human serum samples with the GLP-1 immunogenicity LFA. Sample 300 was found positive and was retested.
Figure 18:
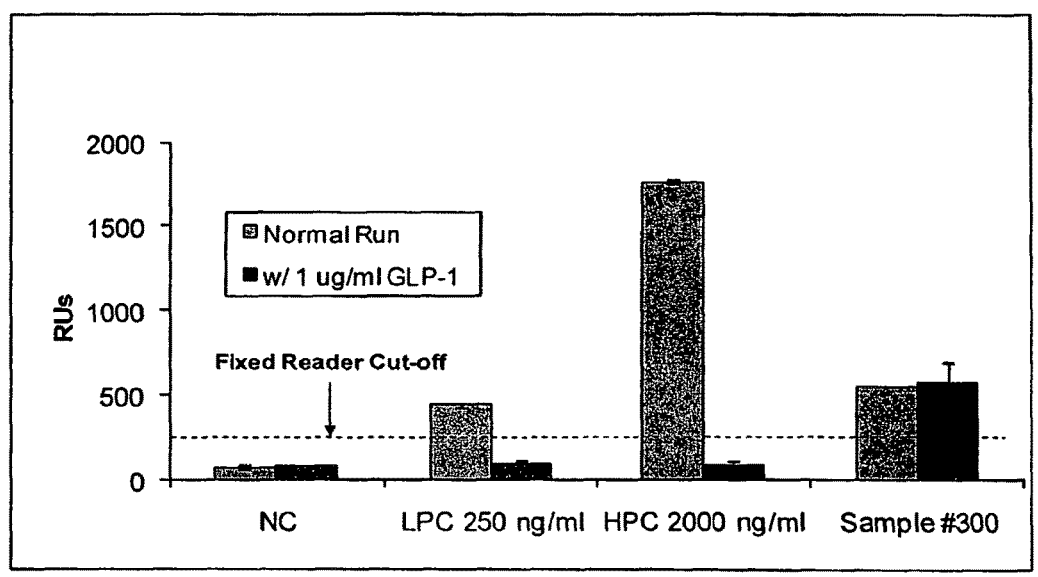
FIG. 18 presents the results of the retesting of an apparent positive obese human patient sample number 300 in a drug depletion assay showing sample 300 to be a false positive.
Figure 19:
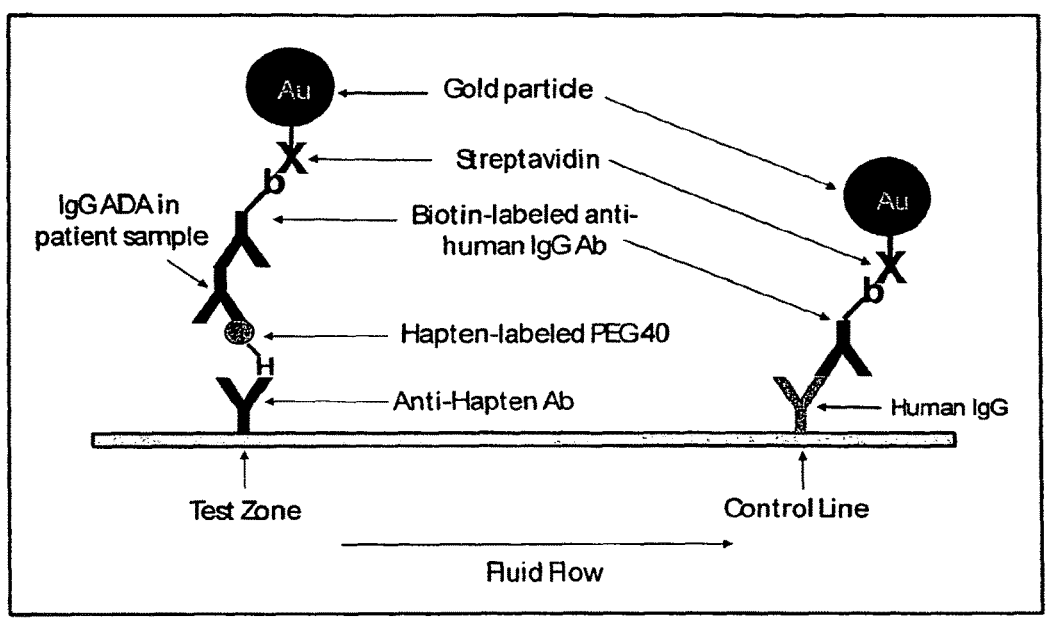
FIG. 19 shows the reaction schematic for one format of an LFA for the identification of IgG isotypes or subclasses.
Figure 20:
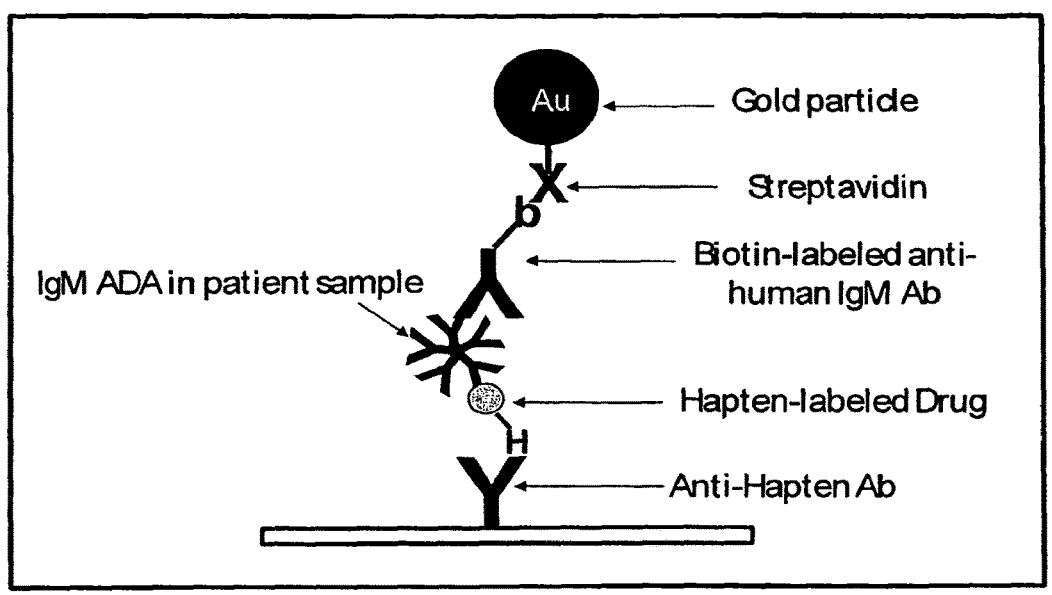
FIG. 20 shows the reaction schematic for one format of an LFA for the identification of IgM isotypes or subclasses of ADAs.
Figure 21:
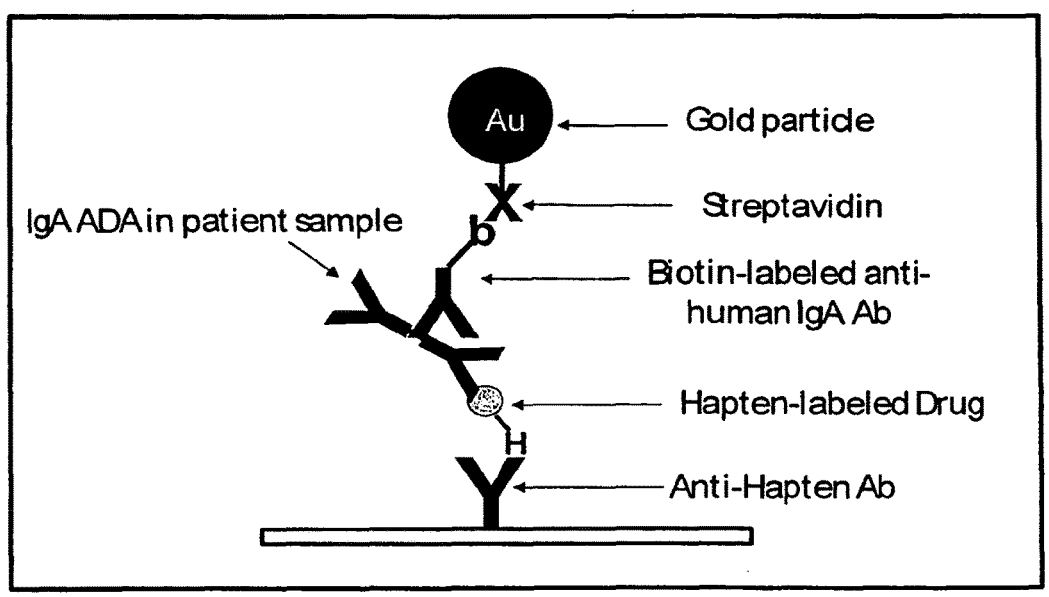
FIG. 21 shows the reaction schematic for one format of an LFA for the identification of IgA isotypes or subclasses of ADAs.
Figure 22:
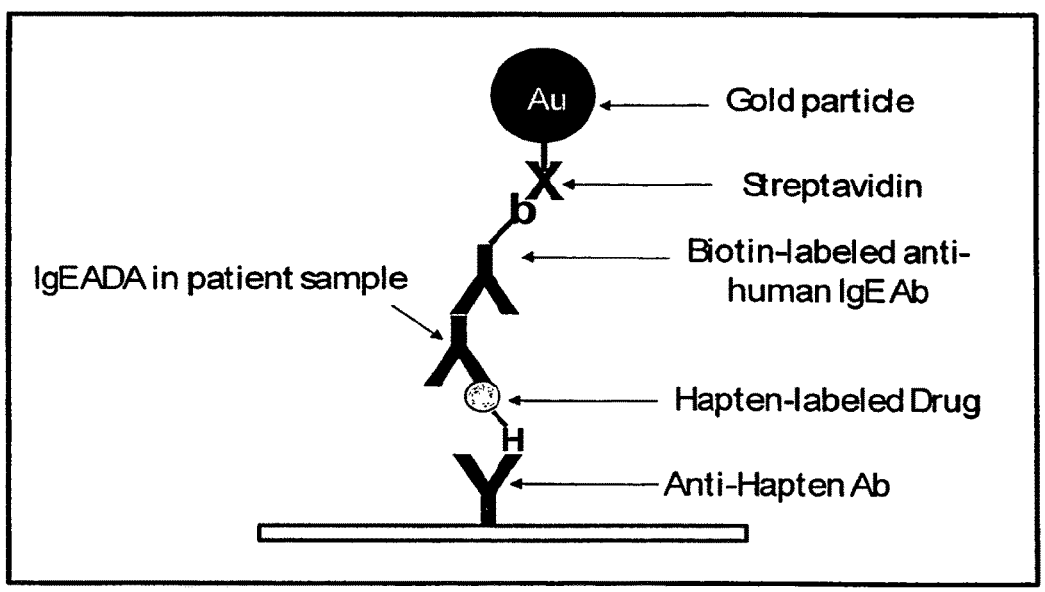
FIG. 22 shows the reaction schematic for one format of an LFA for the identification of IgE isotypes or subclasses of ADAs.

Fifty serum samples from obese patients were tested in the GLP-1 immunogenicity LFA in two separate batches (FIGS. 16 and 17). Only sample 300 was found to be positive. That sample was retested and subjected to the drug depletion assay for confirmation. The results of the confirmation test show that sample 300 is a false positive (FIG. 18).

All references cited herein are herein incorporated by reference in entirety.

REFERENCES

1. Polymer Conjugate Enhanced Bioassays, US Pub. No. 20080200562
2. Symmetrically Branched Polymer Conjugates and Microarray Assays, US Pub. No. 20080114077
3. Asymmetrically branched polymer conjugates and microarray assays, US Pub. No. 20060041058
4. Recommendations for the design and optimization of immunoassays used in the detection of host antibodies against biotechnology products, Mire-Sluis et al. J Immunological Methods 289 (2004) 1-16
5. Comparison ELISA and surface plasmon resonance for assessing clinical immunogenicity of panitumumab, Lofgren et al. J Imm (2007) 7467-7472

We claim:

1. A method of detecting an antibody to an antigen, wherein said antigen comprises a drug of interest (DOI), a food antigen (FA), an environmental antigen (EA) or a tag attached to said DOI, FA or EA, comprising:
   (a) contacting a sample suspected of comprising said antibody to an antigen, to a capture site of a device, said capture site comprising a solid phase comprising an immobilized capture agent, wherein said solid phase comprises a member of a first binding pair and a branched polymer, and said capture agent comprises said antigen and a cognate tag of said member of said first binding pair;
   (b) following step (a), contacting said antigen comprising a member of a second binding pair, to said capture site, wherein said antigen of step (a) and said antigen of step (b) are the same;
   (c) following step (b), contacting a reporter to said capture site, wherein said reporter comprises a cognate tag of said member of said second binding pair and optionally, a branched polymer; and
   (d) following step (c), detecting reporter at said capture site,
   wherein reporter at said capture site correlates with presence of said antibody to said antigen in said sample.

2. The method of claim 1, wherein said solid phase comprises a membrane, a glass micro/nanochannel, a plastic micro/nanochannel, a natural wick, a synthetic wick, microbead particles, nanobead particles or a combination thereof.

3. The method of claim 1, wherein said solid phase comprises a membrane, said membrane comprises nitrocellulose, glass fiber, cotton or polyamide.

4. The method of claim 1, wherein said second binding pair comprises an antibody that binds a hapten.

5. The method of claim 4, wherein said hapten is selected from the group consisting of dinitrophenol, digoxigenin, digoxin, fluorescein, thyroxine, tetrahydrocannabinol, morphine, amphetamine, heroin and a barbiturate.

6. The method of claim 1, wherein said branched polymer comprises a polyethyleneimine.

7. The method of claim 1, wherein said DOI comprises an antigen-binding polypeptide, an antibody, a saccharide, an siRNA, an RNAi or an mRNA.

8. The method of claim 1, wherein said member of said first binding pair comprises a cognate tag of biotin.

9. The method of claim 1, wherein said reporter is selected from the group consisting of an enzyme, a ferritin, a fluorescent or colored microparticle/bead or nanoparticle/bead, a colloid metal, a quantum dot, a magnetic particle, an up-converting phosphorescent particle, an electrochemiluminescent molecule, a compound comprising a transition metal, and a compound comprising a lanthanide metal.

10. The method of claim 1, wherein said DOT is selected from the group consisting of an organic compound, a polypeptide, a polynucleotide, a lipid, a polysaccharide and combinations thereof.

11. The method of claim 1, wherein said tag attached to said DOI, FA or EA is selected from the group consisting of a charged group, an este group, a glycan, a carbohydrate, a water soluble polymer and a synthetic polymer.

12. The method of claim 1, wherein said tag attached to said DOI, FA or EA comprises a polyethylene glycol (PEG) or a polyethyleneoxide (PEO).

13. The method of claim 1, wherein said capture agent comprises a DOI, an FA or an EA.

14. The method of claim 1, wherein said first and/or said second binding pair is selected from the group consisting of an antibody or an antigen-binding portion thereof and an antigen, an avidin/streptavidin/neutravidin and a biotin, a dinitrophenol (DNP) and an anti-DNP antibody, a digoxin and an anti-digoxin antibody, a digoxigenin and an anti-digoxigenin antibody, a hapten and an anti-hapten antibody, a polysaccharide and a polysaccharide binding moiety, a lectin or a receptor, a ligand and a receptor, a fluorescein and an anti-fluorescein antibody, and complementary nucleic acids.

15. The method of claim 1, wherein said branched polymer is selected from the group consisting of a star-shaped polymer, a comb-shaped polymer, a dendrimer, a starburst dendrimer, a combburst dendrigraft, and a hypercomb-branched polymer.

16. The method of claim 1, wherein said branched polymer comprises a polylysine dendrimer or a randomly branched polymer.

17. The method of claim 1, wherein said device comprises a tissue culture plate, a multi-well plate or a combination thereof.

18. The method of claim 1, wherein said detecting reporter comprises a reader.

19. The method of claim 1, wherein the solid phase comprises a bead.

20. The method of claim 1, wherein said capture agent comprises an antibody or an antigen-binding portion thereof.

* * * * *